US009216004B2

(12) United States Patent
Talant

(10) Patent No.: US 9,216,004 B2
(45) Date of Patent: Dec. 22, 2015

(54) ADAM AND EASE MAMMOGRAPHY DEVICE

(71) Applicant: Jesse Talant, Chicago, IL (US)

(72) Inventor: Jesse Talant, Chicago, IL (US)

( * ) Notice: Subject to any disclaimer, the term of this patent is extended or adjusted under 35 U.S.C. 154(b) by 32 days.

(21) Appl. No.: 14/025,812

(22) Filed: Sep. 12, 2013

(65) Prior Publication Data

US 2015/0073254 A1    Mar. 12, 2015

(51) Int. Cl.
| | |
|---|---|
| *A61B 6/00* | (2006.01) |
| *A41C 3/00* | (2006.01) |
| *A61B 5/00* | (2006.01) |
| *A61B 6/03* | (2006.01) |
| *A61B 6/04* | (2006.01) |
| *A61B 8/08* | (2006.01) |
| *A61B 8/00* | (2006.01) |

(52) U.S. Cl.
CPC .............. *A61B 6/502* (2013.01); *A41C 3/0064* (2013.01); *A61B 5/0091* (2013.01); *A61B 6/4417* (2013.01); *A61B 5/6804* (2013.01); *A61B 6/032* (2013.01); *A61B 6/0414* (2013.01); *A61B 8/0825* (2013.01); *A61B 8/4227* (2013.01)

(58) Field of Classification Search
CPC .... A61B 8/4455; A61B 8/4461; A61B 8/461; A61B 5/0091; A61B 5/6804; A61B 6/502; A61B 8/0825; Y10S 128/915; Y10S 128/916; A41C 3/00; A41C 3/005; A41C 3/0064
See application file for complete search history.

(56) References Cited

U.S. PATENT DOCUMENTS

| | | | |
|---|---|---|---|
| 4,075,883 A | 2/1978 | Glover et al. | |
| 4,130,112 A | 12/1978 | Frazer et al. | |
| 4,509,368 A | 4/1985 | Whiting et al. | |
| 5,803,082 A | 9/1998 | Stapleton et al. | |
| 6,086,247 A * | 7/2000 | von Hollen | 374/137 |
| 6,146,377 A * | 11/2000 | Lee et al. | 606/13 |
| 6,179,786 B1 | 1/2001 | Young et al. | |
| 6,319,201 B1 * | 11/2001 | Wilk | 600/437 |
| 6,389,305 B1 * | 5/2002 | Deban et al. | 600/427 |
| 6,478,739 B1 * | 11/2002 | Hong | 600/437 |
| 6,482,158 B2 | 11/2002 | Mault et al. | |
| 6,498,652 B1 | 12/2002 | Varshneya et al. | |
| 6,790,178 B1 | 9/2004 | Mault et al. | |
| 7,221,814 B2 | 5/2007 | Allsop et al. | |
| 7,684,601 B2 | 3/2010 | Iddan | |

(Continued)

FOREIGN PATENT DOCUMENTS

| | | |
|---|---|---|
| CN | 103415258 A | 11/2013 |
| DE | 3136037 A1 | 4/1982 |

(Continued)

*Primary Examiner* — Matthew F DeSanto

(57) ABSTRACT

Two styles of The Mammography Device are intended, brassiere style (typically for females) and breastplate style (typically for males). The Device should be manufactured to include highly variable cup or mold sizes that will conform to the breast and torso snugly without tightness and use Sensors and Mesh Lines to "read" through breast tissue. Secondary Torso Connectors enhance sizing variability. The Device will have a Vacuum Ability, which allows the Conforming Mesh to be customized to individuals. The Device will create a more comfortable screening for breast tissue anomalies than current methods. The Device may be manufactured to be recyclable; each part should be soft. The Device may be ground for electricity via Grounding Points at its right or left Horn. The communication port on The Device may be used to connect it, if not using wireless communications, from its Rim to a computer.

2 Claims, 31 Drawing Sheets

(56) References Cited

U.S. PATENT DOCUMENTS

Figure 1:
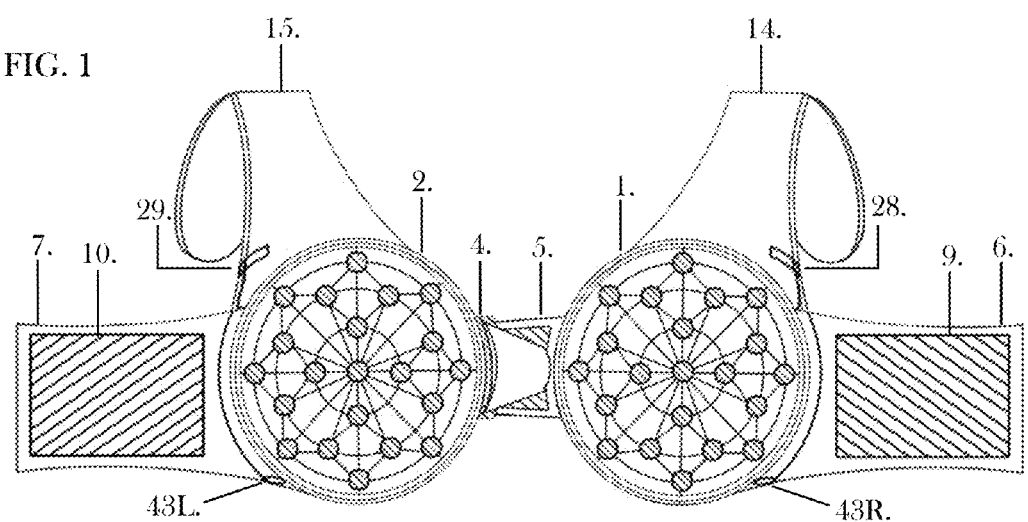

| | | |
|---|---|---|
| 7,742,561 B2 | 6/2010 | Ueki |
| 7,781,724 B2 | 8/2010 | Childers et al. |
| 7,828,732 B2 | 11/2010 | Wang et al. |
| 8,206,324 B2 | 6/2012 | Kurono et al. |
| 8,818,478 B2 * | 8/2014 | Scheffler et al. ............. 600/388 |
| 2002/0138120 A1 | 9/2002 | Whitehurst |
| 2004/0236267 A1 | 11/2004 | Pierce |
| 2005/0020921 A1 * | 1/2005 | Glassell et al. ............. 600/463 |
| 2006/0262898 A1 * | 11/2006 | Partain et al. ................. 378/37 |
| 2006/0270930 A1 * | 11/2006 | Brasile ......................... 600/410 |
| 2007/0092059 A1 * | 4/2007 | Wayne Eberhard et al. .... 378/37 |
| 2007/0276229 A1 * | 11/2007 | Adler .......................... 600/426 |
| 2010/0067770 A1 * | 3/2010 | Persson et al. ............... 382/132 |
| 2010/0094119 A1 * | 4/2010 | Yu et al. ....................... 600/411 |
| 2010/0286546 A1 | 11/2010 | Tobola et al. |
| 2011/0105865 A1 | 5/2011 | Yu et al. |
| 2011/0109898 A1 | 5/2011 | Froggatt et al. |
| 2011/0245653 A1 * | 10/2011 | Varahramyan et al. ....... 600/407 |
| 2012/0063123 A1 | 3/2012 | Redpath et al. |
| 2012/0209124 A1 * | 8/2012 | Shieh et al. .................... 600/476 |
| 2013/0225988 A1 * | 8/2013 | Mahfouz ....................... 600/430 |
| 2013/0267850 A1 * | 10/2013 | Berman ......................... 600/443 |
| 2013/0281815 A1 | 10/2013 | Varadan |
| 2014/0236003 A1 * | 8/2014 | Hielscher et al. ............. 600/428 |

FOREIGN PATENT DOCUMENTS

| | | |
|---|---|---|
| DE | 19926446 A1 | 1/2000 |
| EP | 0105812 A1 | 3/1986 |
| EP | 1750586 A2 | 2/2007 |
| WO | WO-83/02053 | 6/1983 |
| WO | WO-03103500 A1 | 12/2003 |
| WO | WO-2007146101 A2 | 12/2007 |
| WO | WO-2012168836 A2 | 1/2013 |
| WO | WO-2013177370 A1 | 11/2013 |
| WO | WO-2014015260 A1 | 1/2014 |

* cited by examiner

FIG. 3
FIG. 3A
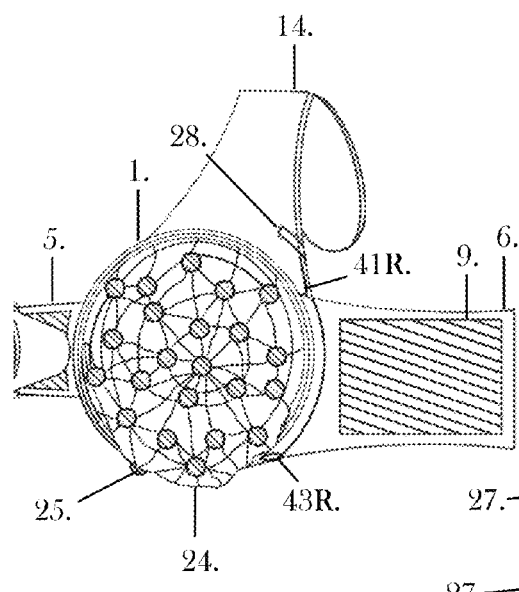
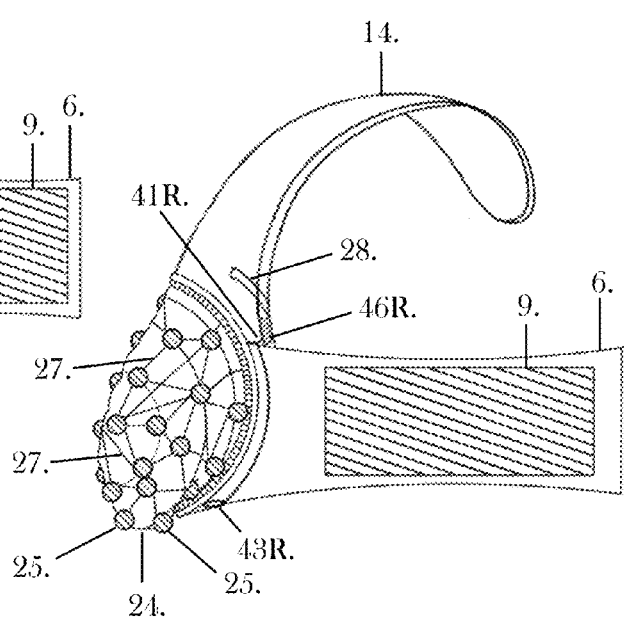

FIG. 10
FIG. 10A
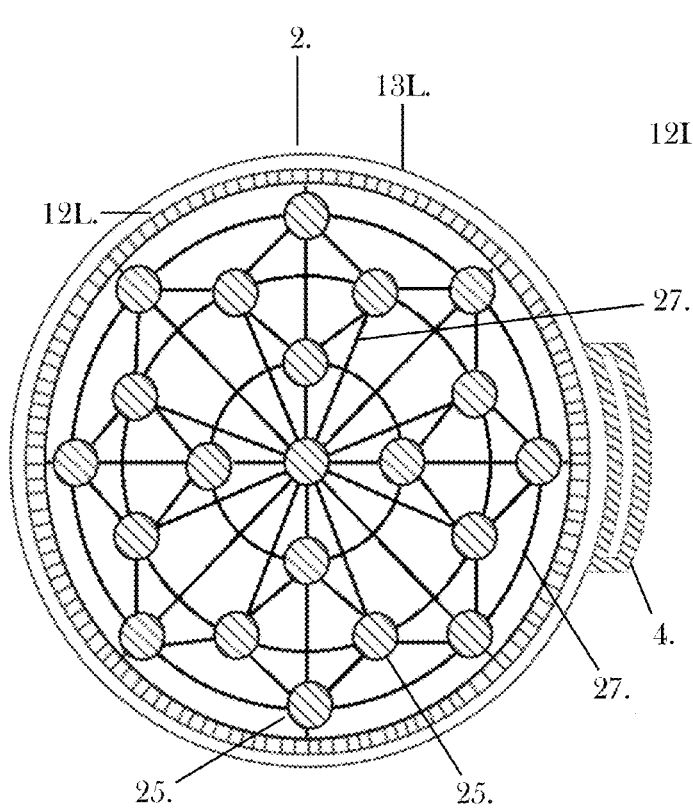
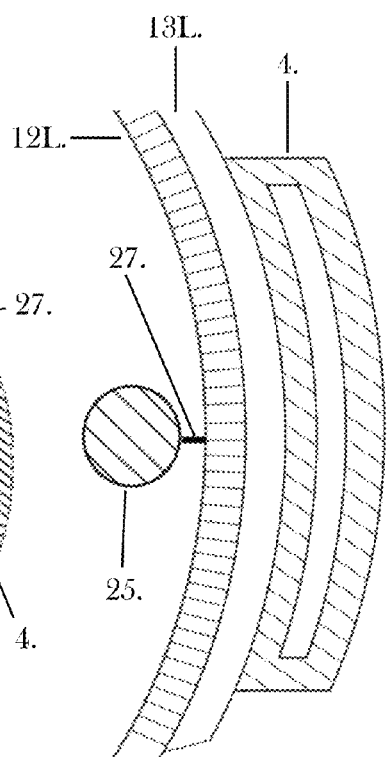

24.

FIG. 27
FIG. 27A
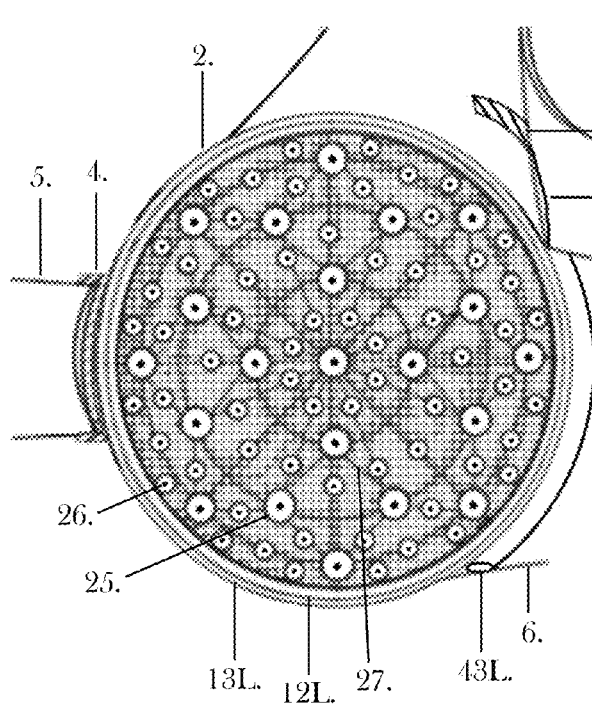
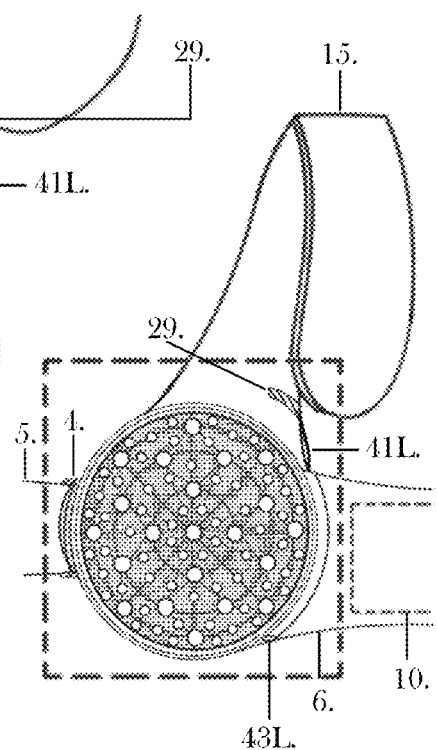

FIG. 28
FIG. 28A
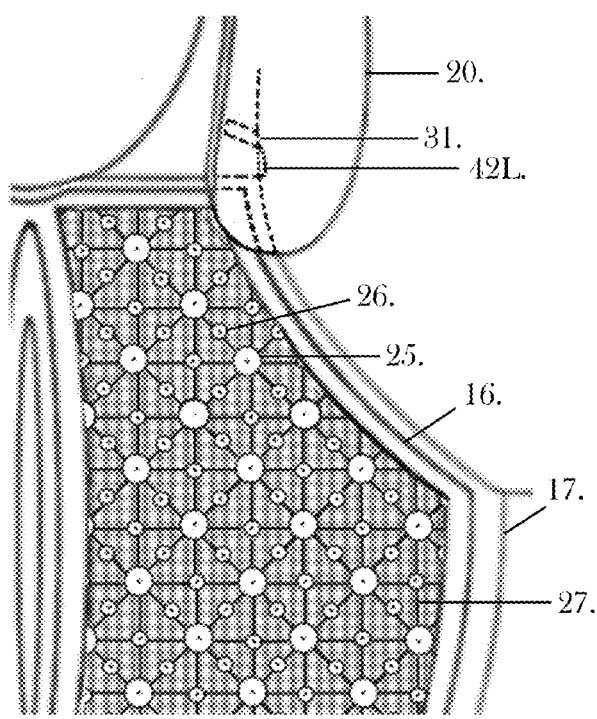
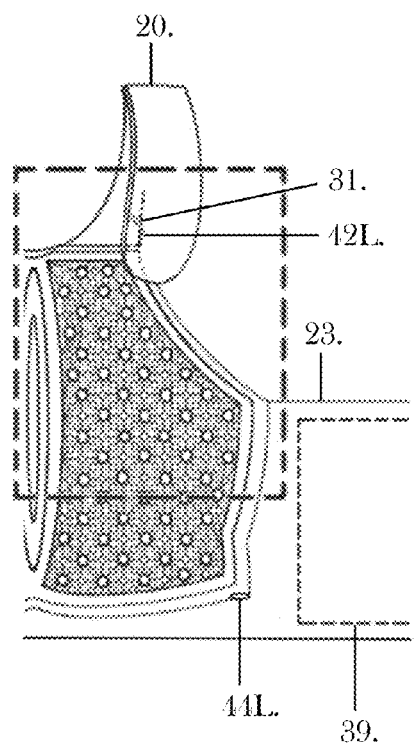

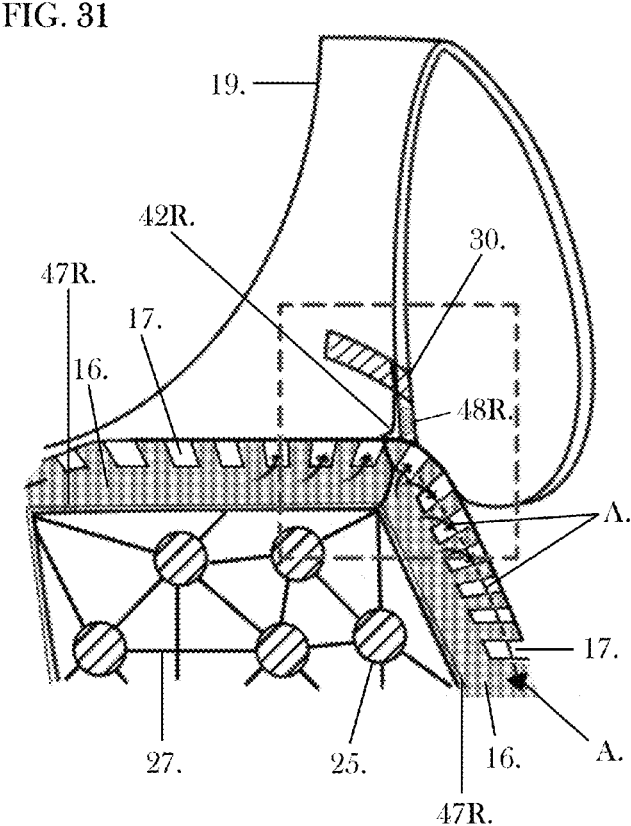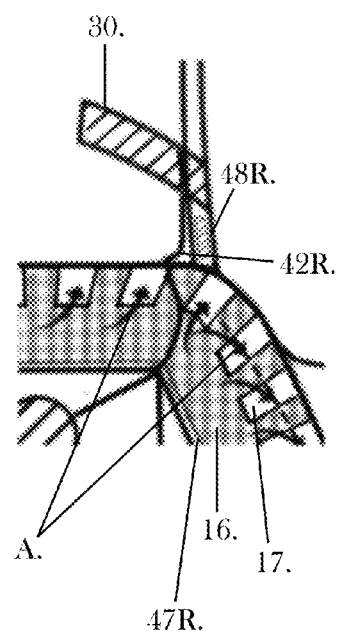

ADAM AND EASE MAMMOGRAPHY DEVICE

CROSS REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Not Applicable

BACKGROUND OF THE INVENTION

Cancer affects thousands of persons worldwide per year and breast cancer is a type of cancer that is often not routinely checked for until it is in its late stages, because of the painful and embarrassing processes used to detect it. One of the current processes that comes to mind involve intense pressing of a patient's breasts in between two panels, another involves repeated pressure being placed upon a patient's breasts with a hand held machine. The Mammography Device will employ a markedly more comfortable method than either of the two prior described ones. I thought of The Mammography Device in the hopes that people would respond positively to it and that it would encourage them be examined sooner and to try something dynamic, that would empower them and perhaps make them feel less like they were physically at the mercy of a machine. This product also recognizes that breast cancer can occur in both the female and male sexes, no matter their age, background or body size.

(1) Field of the Invention
Medical Device
(2) Description of Related Art Including Information Disclosed Under 37 CFR 1.97 and 1.98.

BRIEF SUMMARY OF THE INVENTION

The purpose of this product is to make mammography more comfortable and less of a humiliating experience, which may cause persons to get more timely and more frequent examinations and possibly prevent death. This product was also created to be highly customizable and comfortable to the individual using it.

The Mammography Device is meant to fill the need for comfort and flexibility to patients using it, whether female or male, whether individuals with gynecomastia (males with abnormally larger breasts) to females with mammary hypoplasia, (abnormally smaller breasts). The Device makes an attempt to fit individuals on every part of the spectrum, including persons with macromastia (abnormally larger breasts). Current machines in use in examination settings around the world cause, or can cause, discomfort and pain to the user, not to mention embarrassment, because pressure of some kind is needed to be applied to an individual's breasts for current machines to "take a reading". The Mammography Device may all but eliminate the radiation currently expended in some mammography techniques, making it not only smaller and more comfortable to use, but safer. The Mammography Device was created not only to provide a far less painful experience, but also to provide thorough and accurate first time mammographs, hopefully reducing the need for repeated examinations and speeding the process of initial diagnosis, if any abnormalities are discovered. The Mammography Device is intended to be manufactured in two different styles: The Device for females and the Device for males. These styles are herein described as the Device for males, the Device for females, or the Device, for brevity's sake, from now on. The Device's small comparative size is also potentially space and money saving, versus some of the current products in use as of this writing. Each of The Device's molds or cups is meant to be hypo-allergenic which prevents skin irritation, especially in sensitive individuals; and each mold or cup is durable enough to be sanitized before and after each use, with a sanitizing wipe. The Device may also be constructed of materials that can be recycled immediately instead of being reused. The sizes that The Device should be produced in should range from considerably small to considerably large and comfortably accommodate thinner patients, female or male and larger patients, female or male. (Please note that the illustrations in this application are not to scale; parts such as the Primary Torso Connectors on The Device have been extremely foreshortened to fit the page.)

BRIEF DESCRIPTION OF THE SEVERAL VIEWS OF THE DRAWING(S)

Figure 1A:
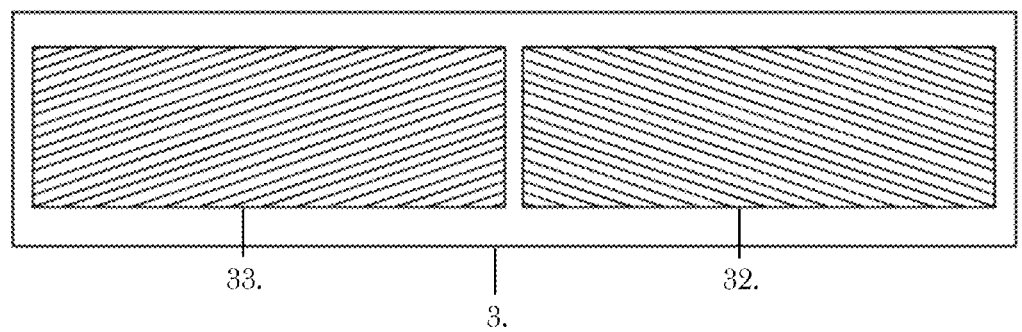
Figure 2:
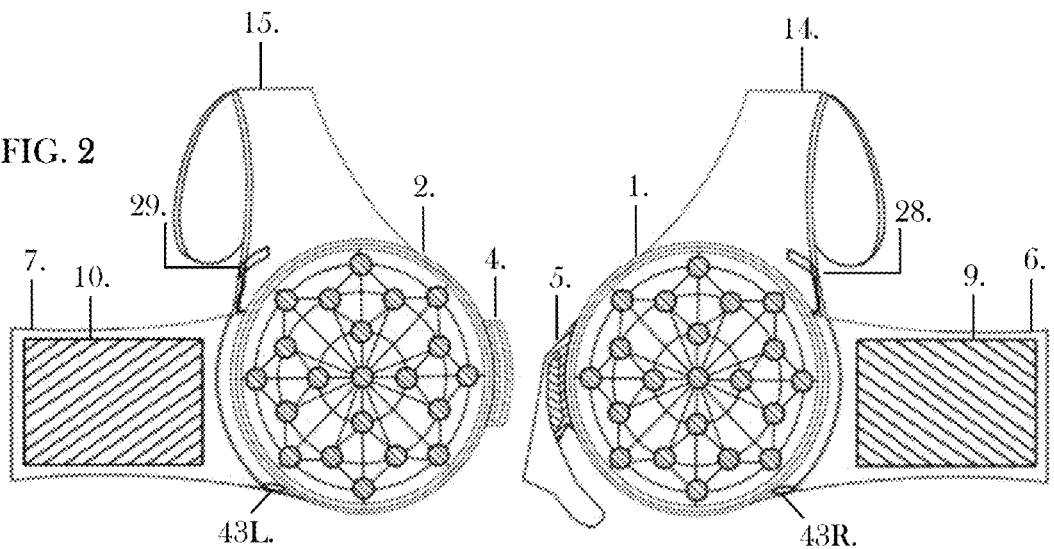
Figure 2A:
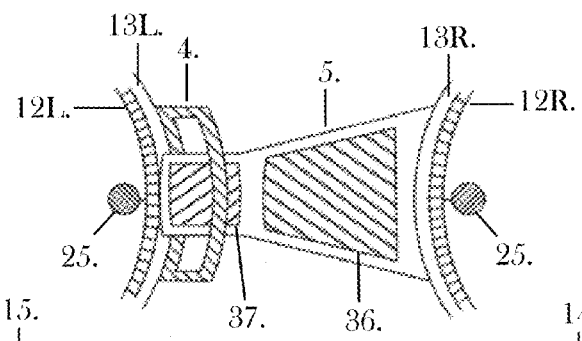
Figure 2B:
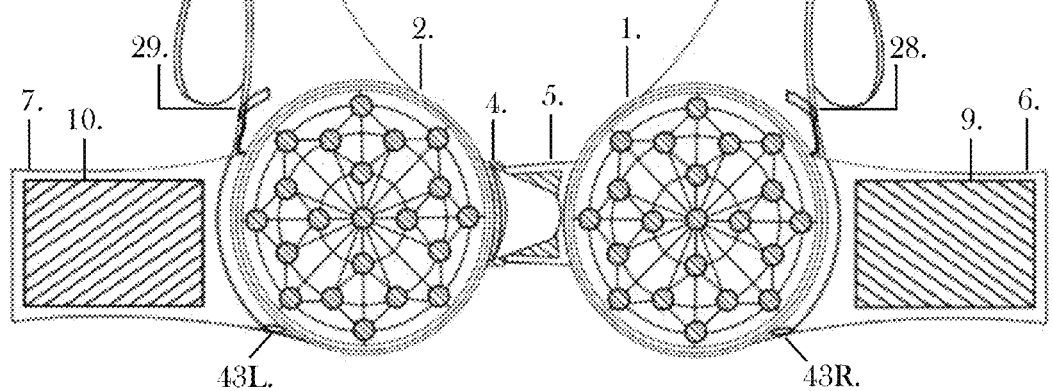
Figure 4:
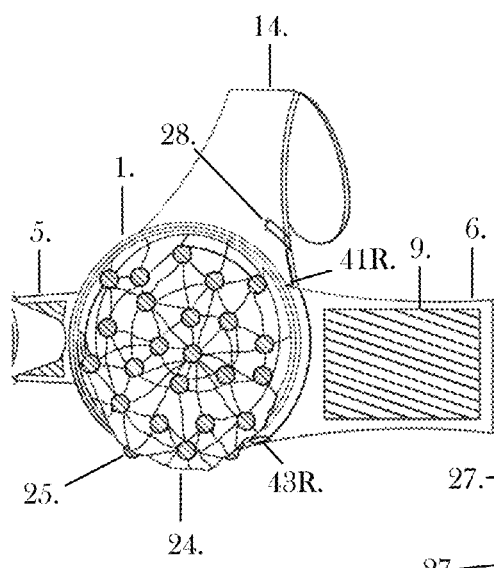
Figure 4A:
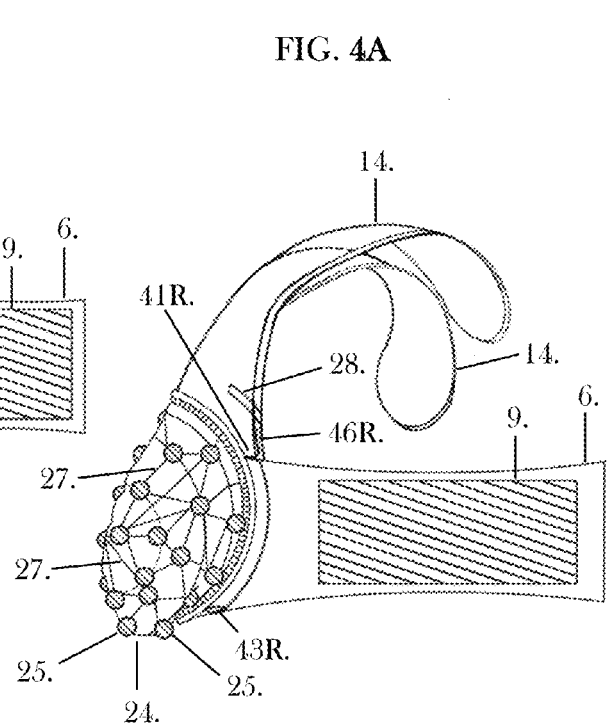
Figure 5:
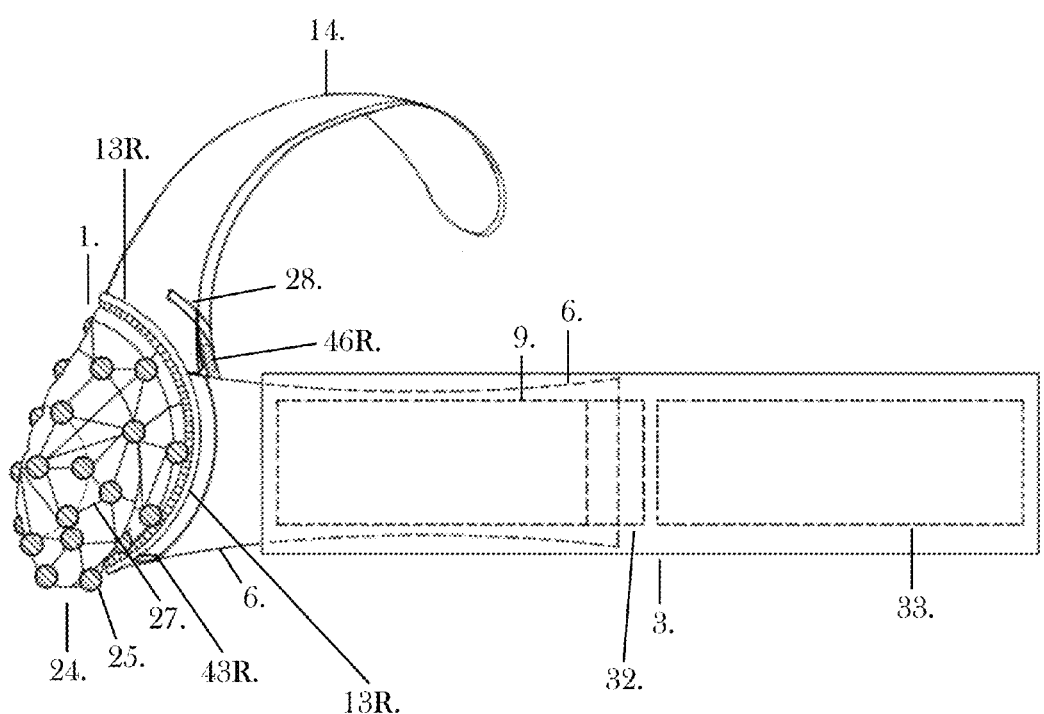
Figure 6:
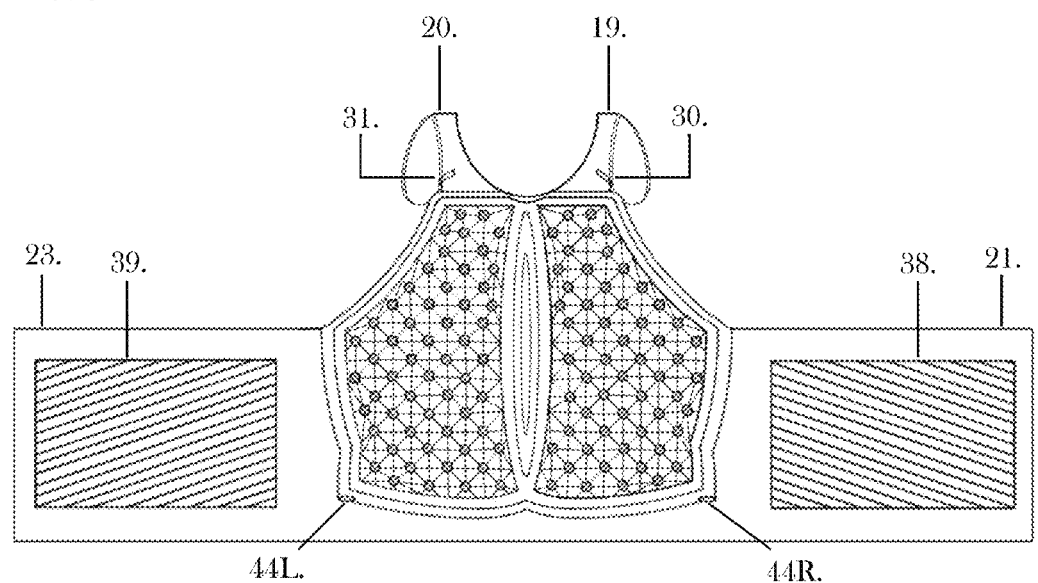
Figure 6A:
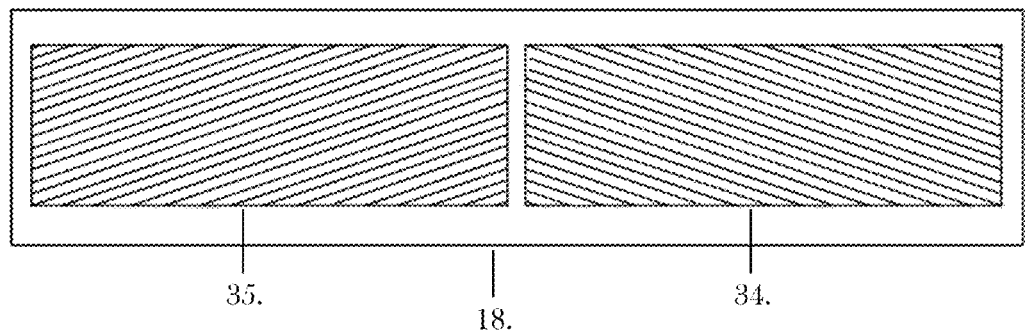
Figure 7:
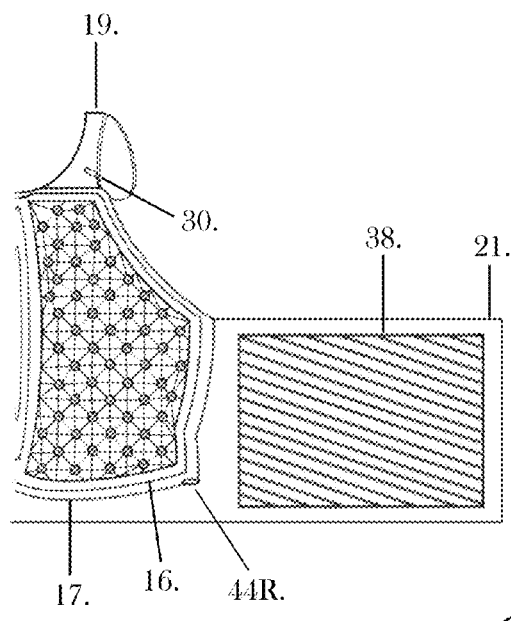
Figure 7A:
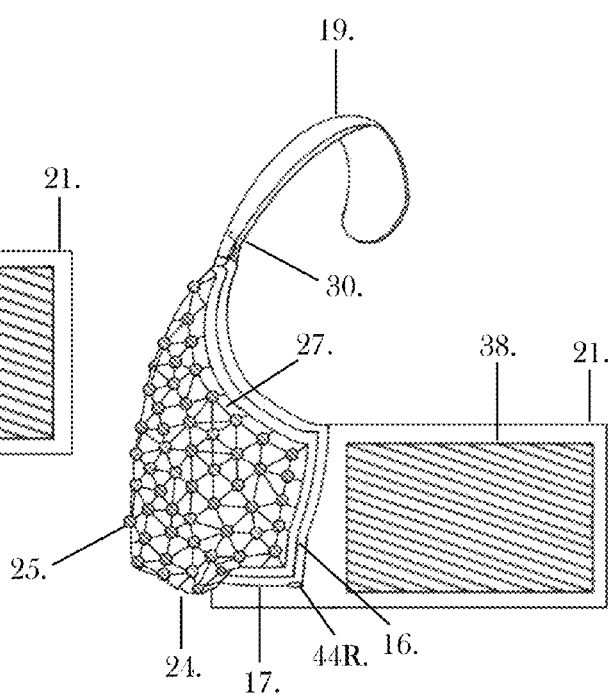
Figure 8:
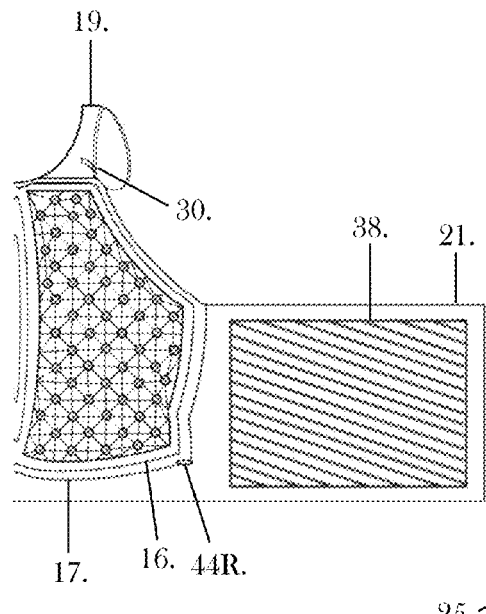

FIG. 1, the front view of the Mammography Device for females.
FIG. 1A, the front view of the Secondary Torso Connector.
FIG. 2, the front view of the Device for females with the Sternum Connector open.
FIG. 2A, a close up of the Sternum Connector and Sternum Connector Flap.
FIG. 2B, the front view of the Device for females with the Sternum Connector closed.
FIG. 3, the front view of the Device for females' left cup or mold.
FIG. 3A, the left side view of the Device for females with static Horn.
FIG. 4, the front view of the Device for females' left cup or mold.
FIG. 4A, the left side view of the Device for females with flexing Horn.
FIG. 5, the left side view of the Device for females attached to a Secondary Torso Connector.
FIG. 6, the front view of the Device for males.
FIG. 6A, the front view of the Secondary Torso Connector.
FIG. 7, the front view of the Device for males' left cup or mold.
FIG. 7A, the left side view of the Device for males with static Horn.
FIG. 8, the front view of the Device for males' left cup or mold.

Figure 8A:
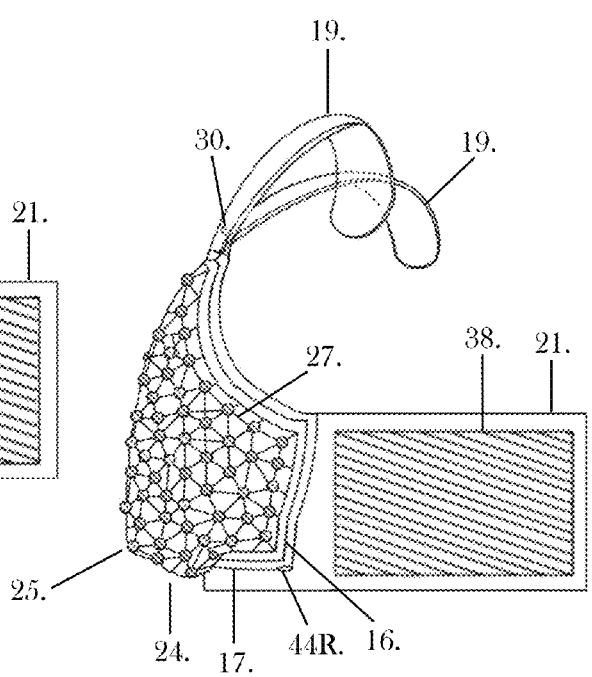

FIG. 8A, the left side view of the Device for males with flexing Horn.

Figure 9:
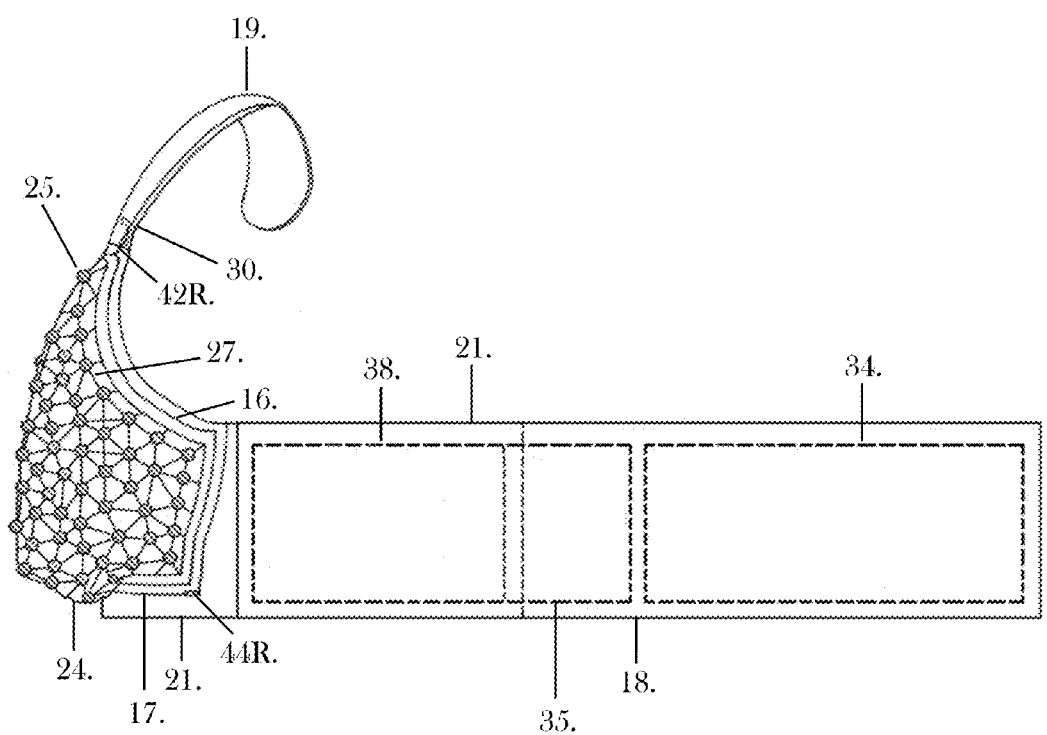

FIG. 9, the left side view of the Device for males attached to a Secondary Torso Connector.

FIG. 10, close up of the Device for females' right cup.

FIG. 10 A, close up of the Device for females' Sternum Connector.

Figure 11:
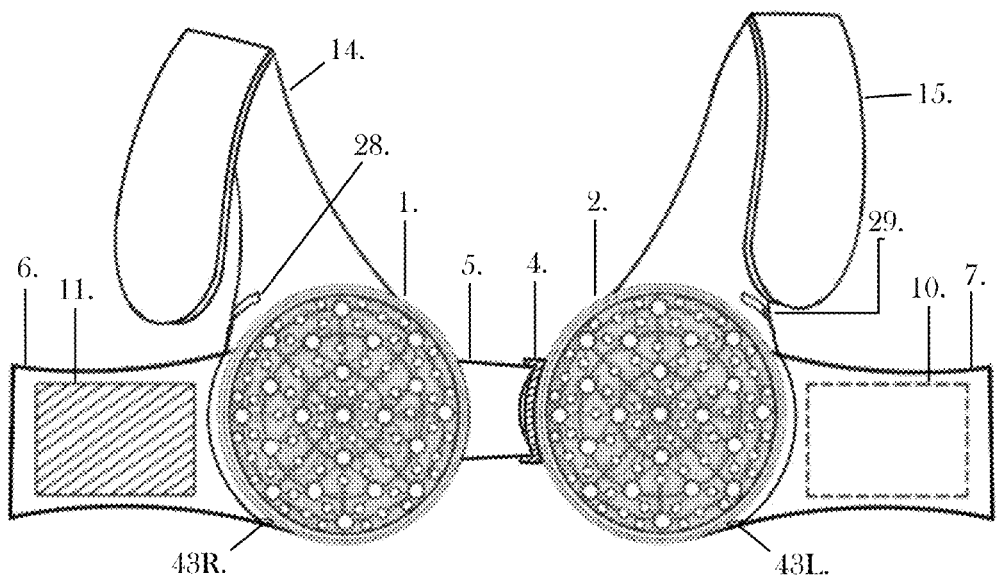

FIG. 11, the Device for females' rear view.

Figure 11A:
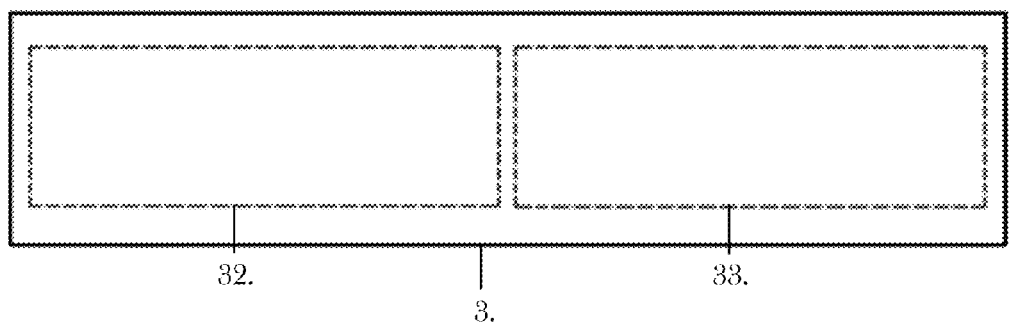

FIG. 11A, the Secondary Torso Connector rear view.

Figure 12:
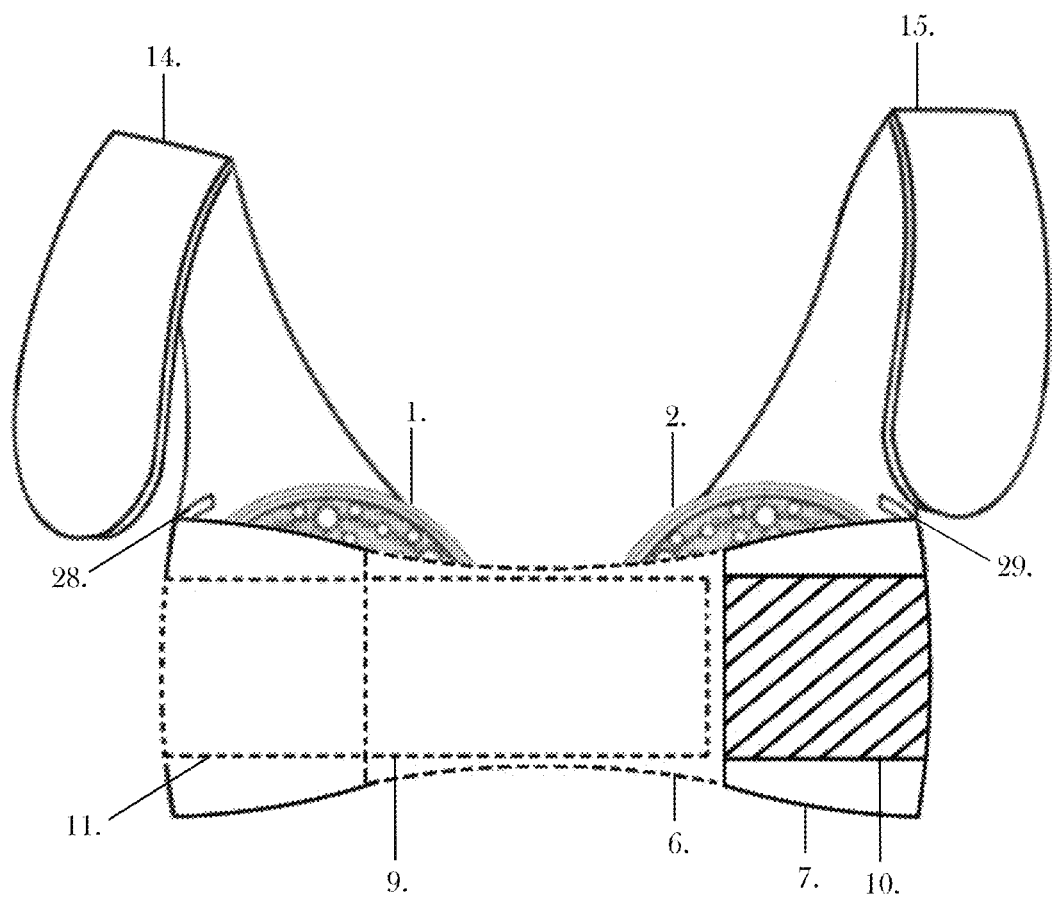

FIG. 12, the Device for females rear view, closed.

Figure 13:
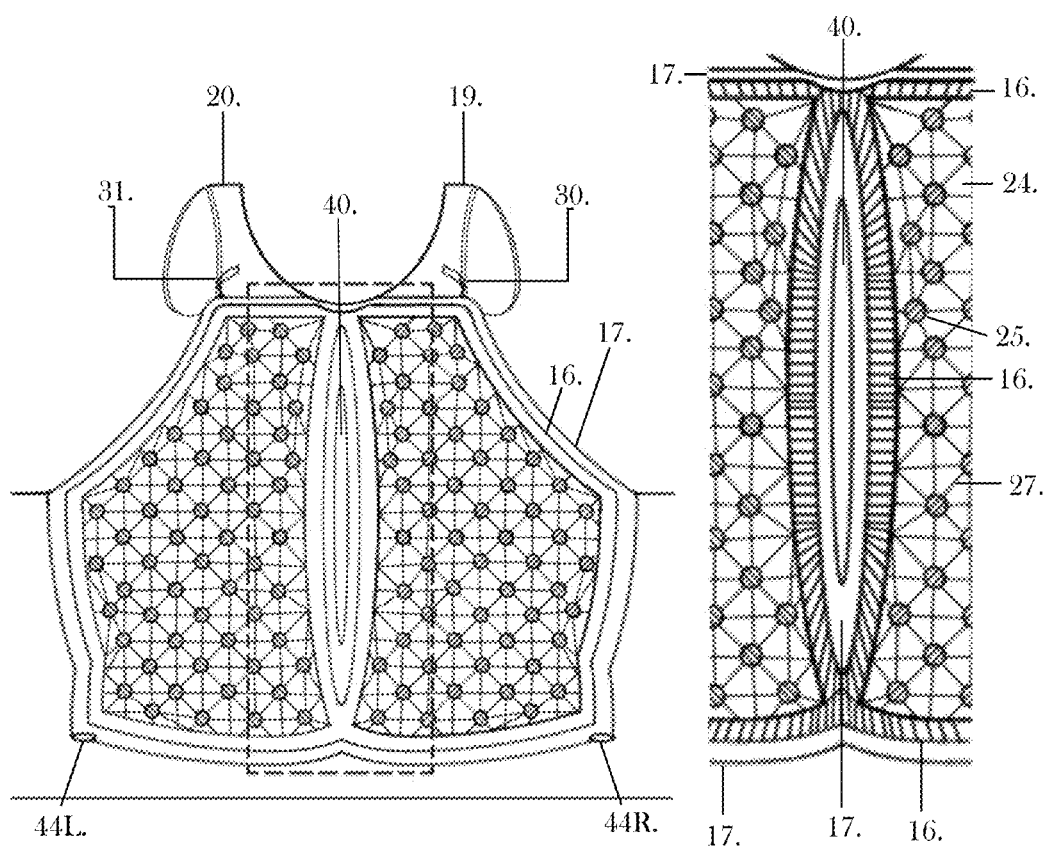

FIG. 13, the Device for males, front center view.

FIG. 13A, the Device for males, front center close up.

Figure 14:
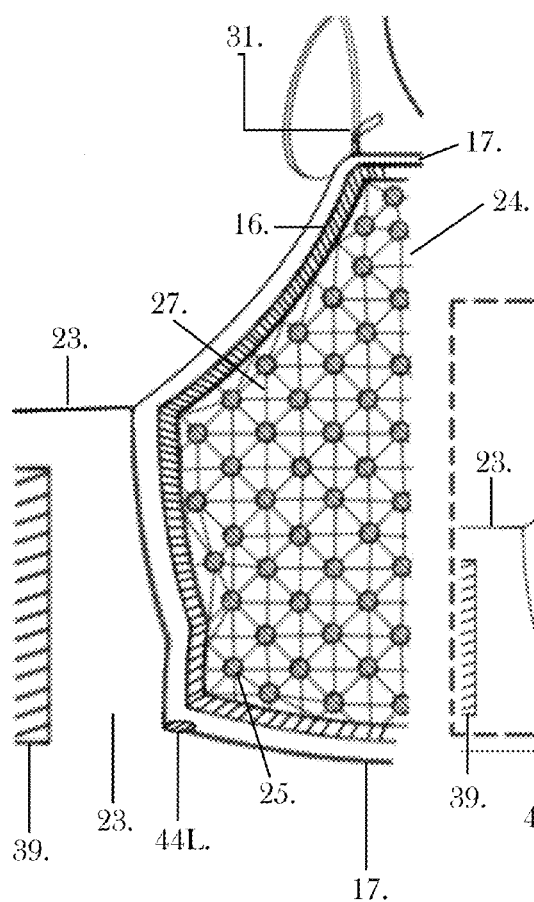

FIG. 14, the Device for males close up at right.

Figure 14A:
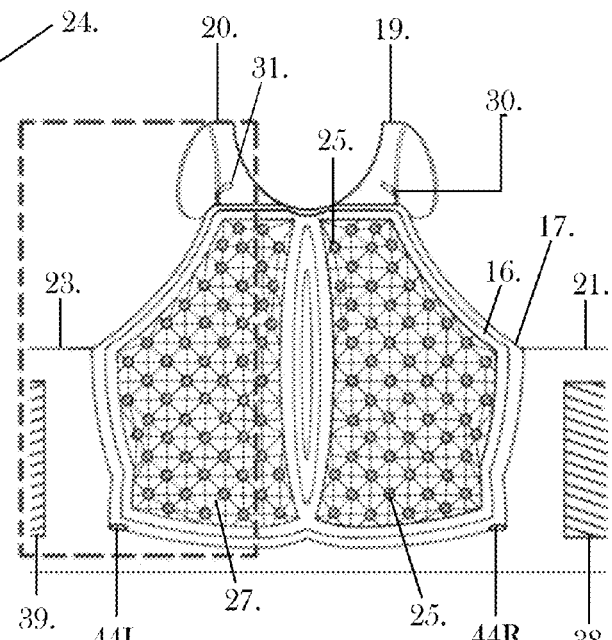

FIG. 14A, the Device for males front center view.

Figure 15:
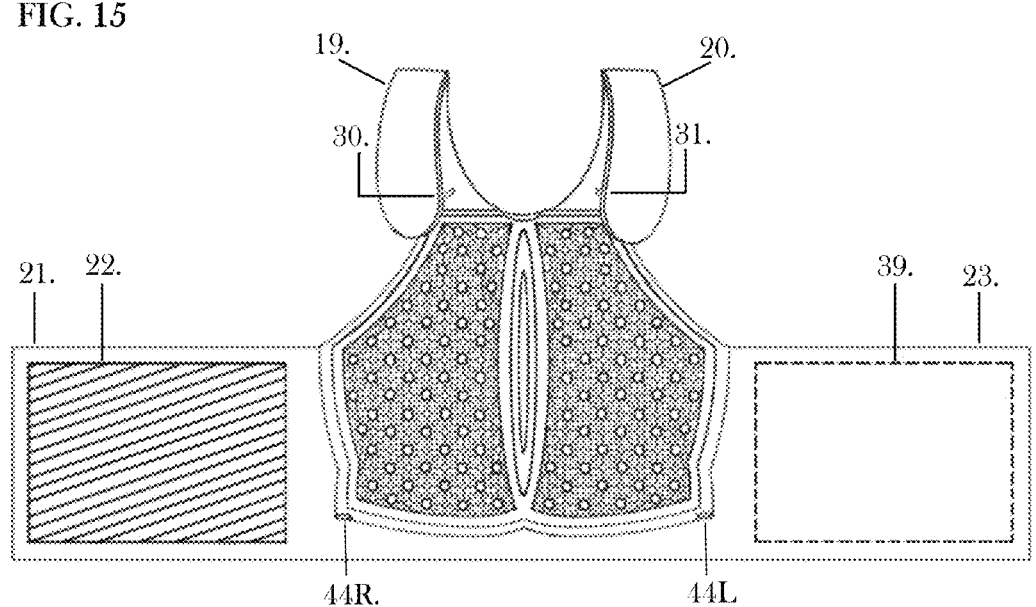

FIG. 15, the Device for males rear view.

Figure 15A:
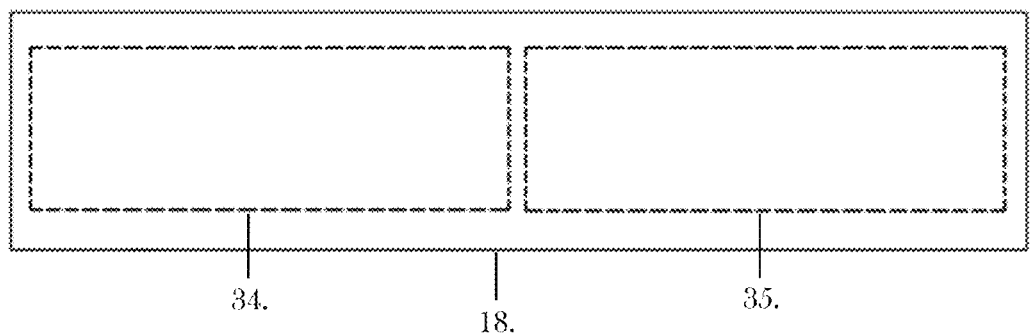

FIG. 15A, a Secondary Torso Connector at rear.

Figure 16:
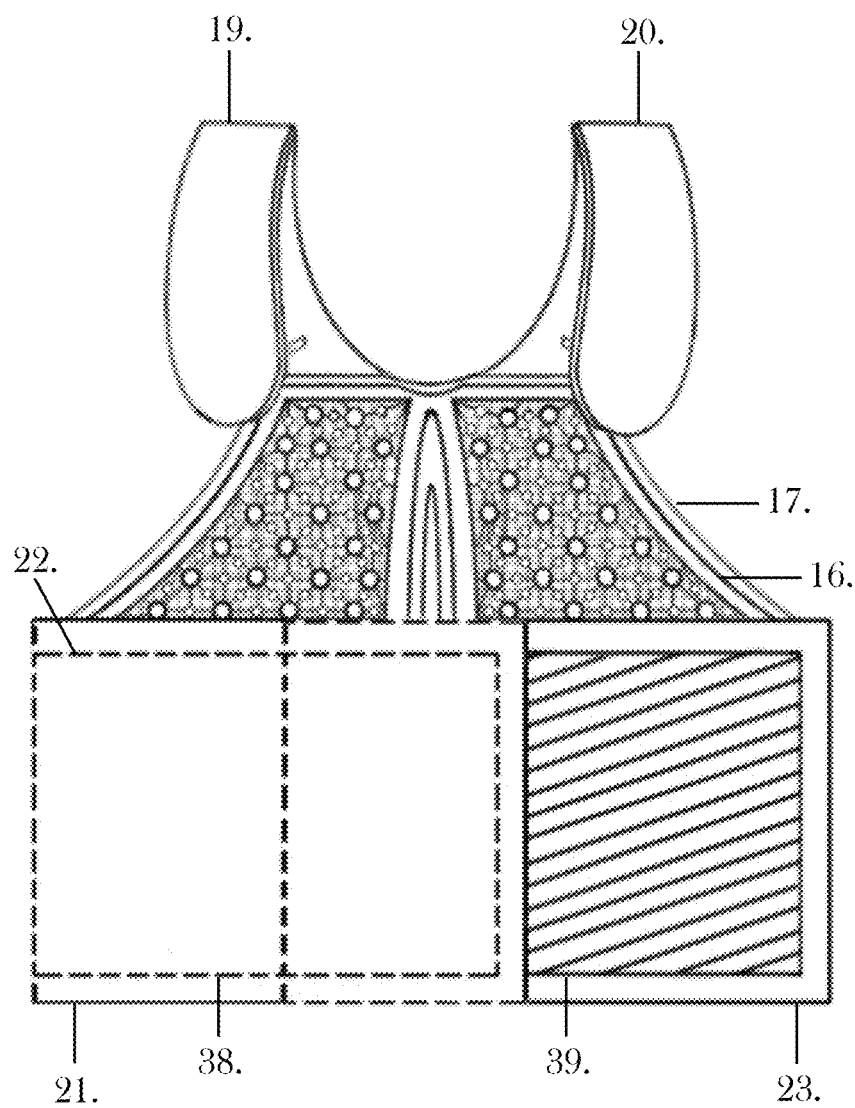

FIG. 16, the Device for males rear view, closed.

Figure 17:
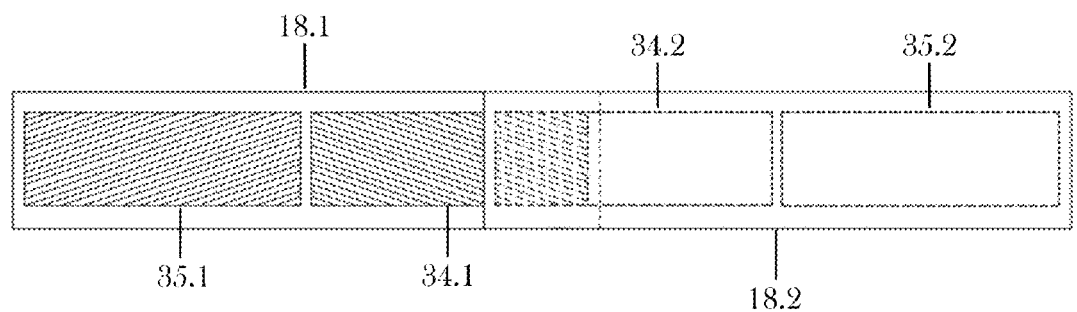

FIG. 17, two Secondary Torso Connectors daisy chained.

Figure 18:
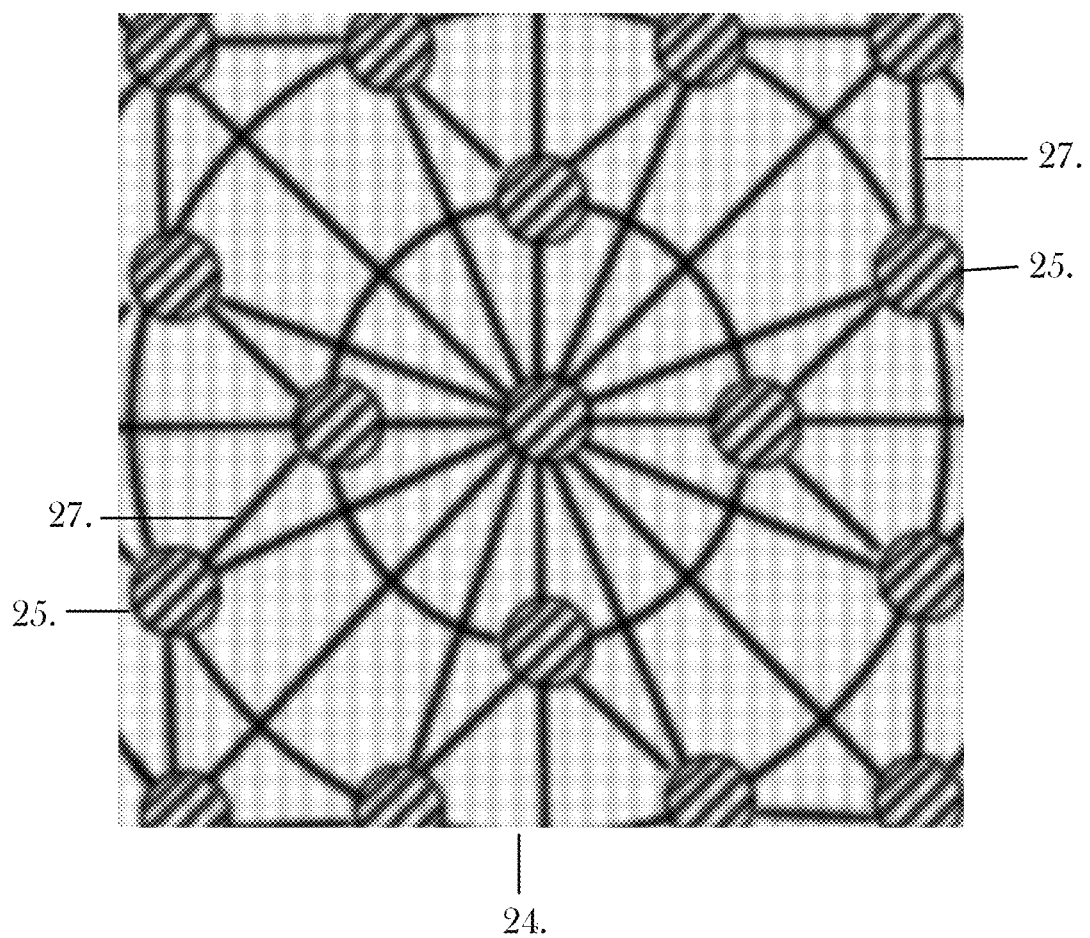

FIG. 18, extreme close up of Sensors on the Device for females' front right cup.

Figure 19:
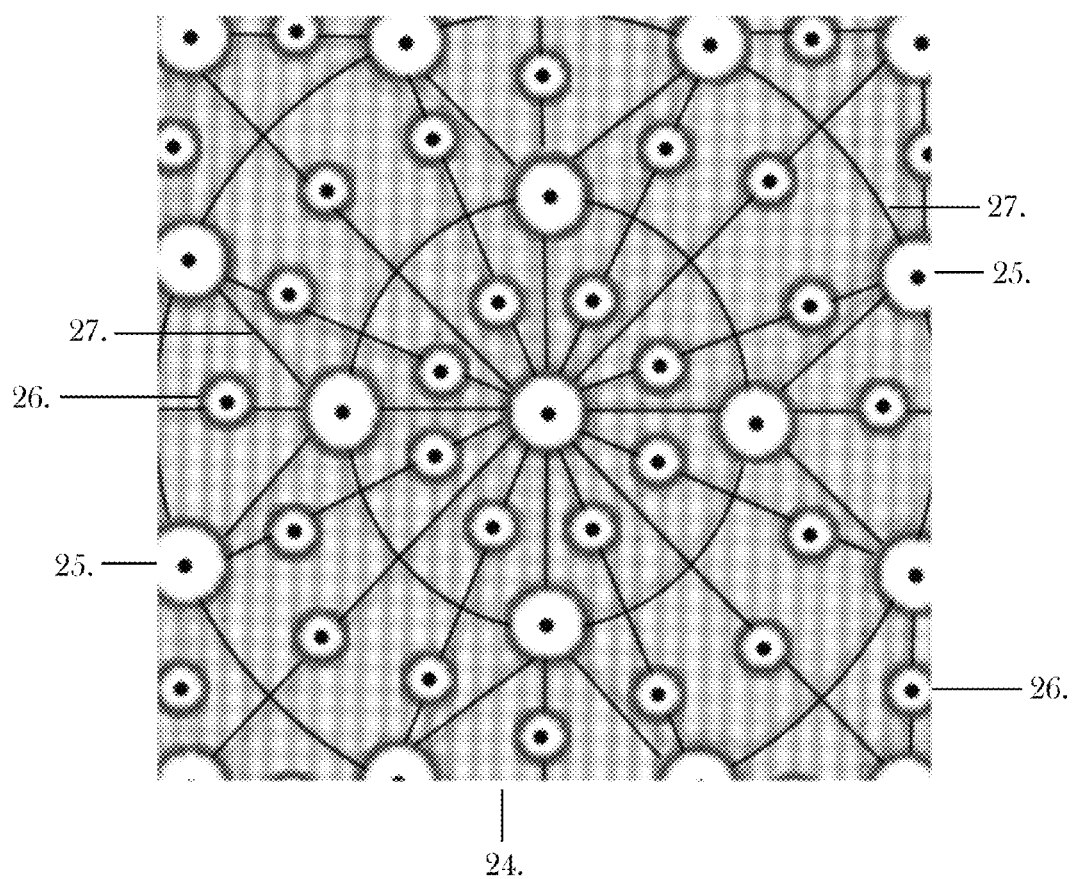

FIG. 19, extreme close up of Sensors on the Device for females' rear right cup.

Figure 20:
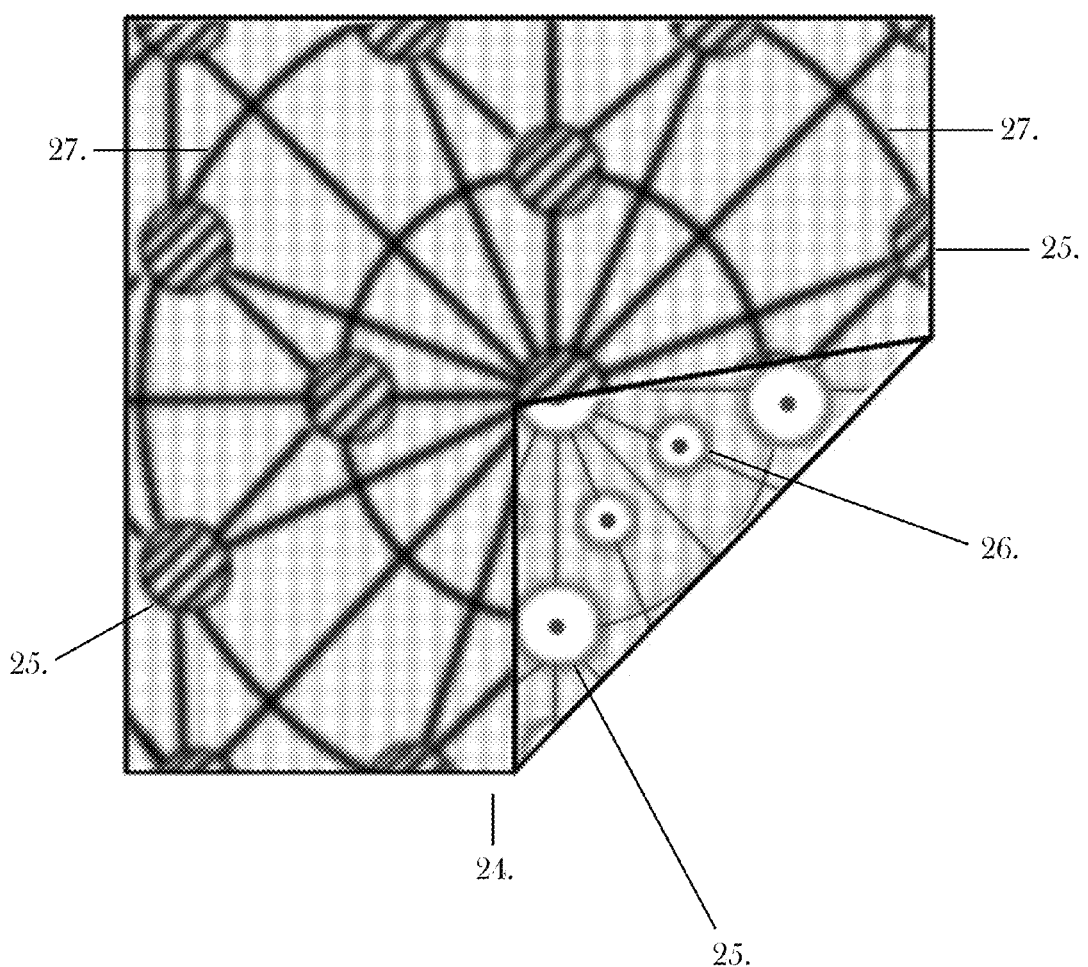

FIG. 20, extreme close up of Sensors on the Device for females' right cup, front and back.

Figure 21:
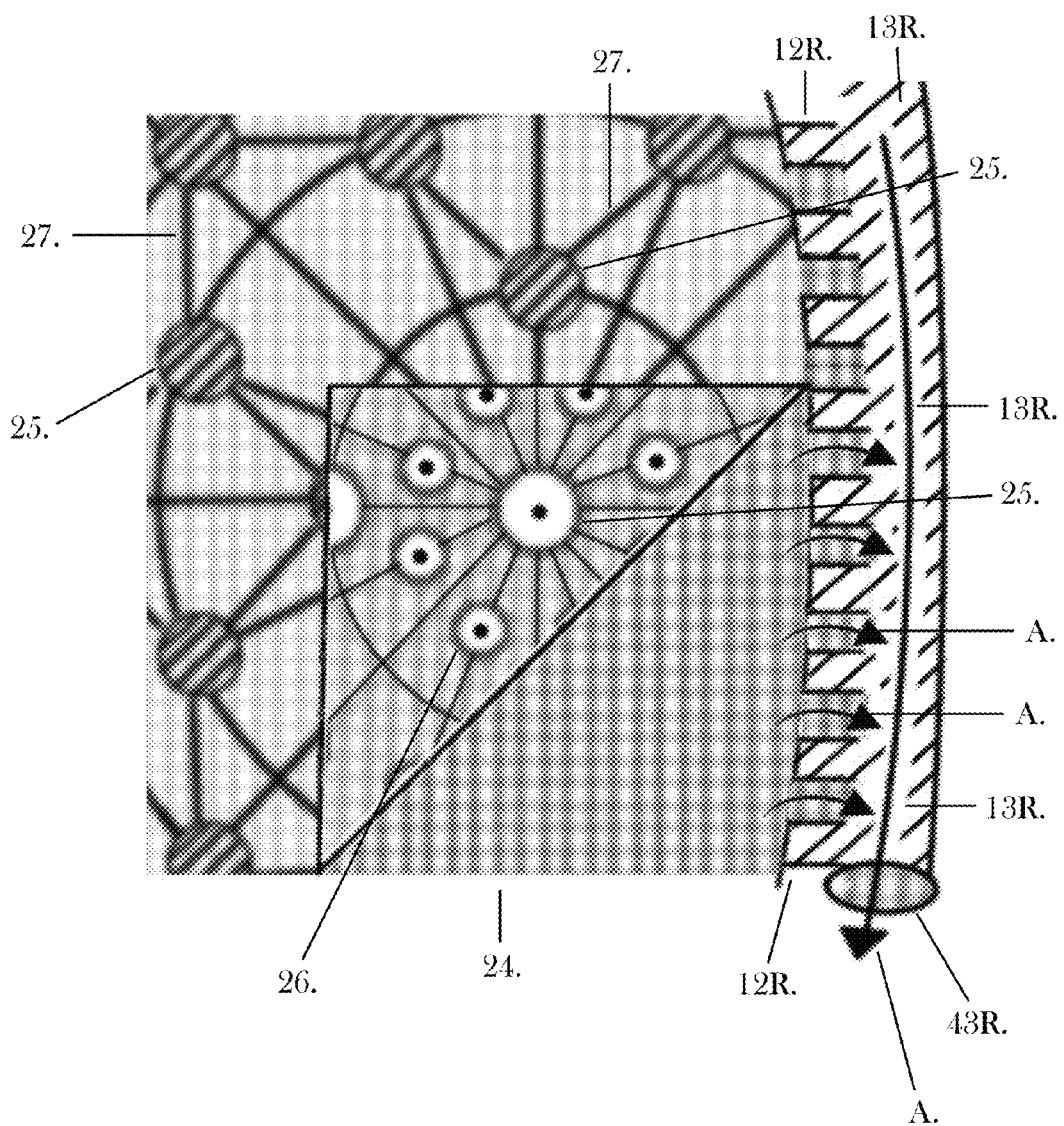

FIG. 21, extreme close up of Sensors on the Device for females' right cup, front and back, with Conforming Mesh and Vacuum Ability views.

Figure 22:
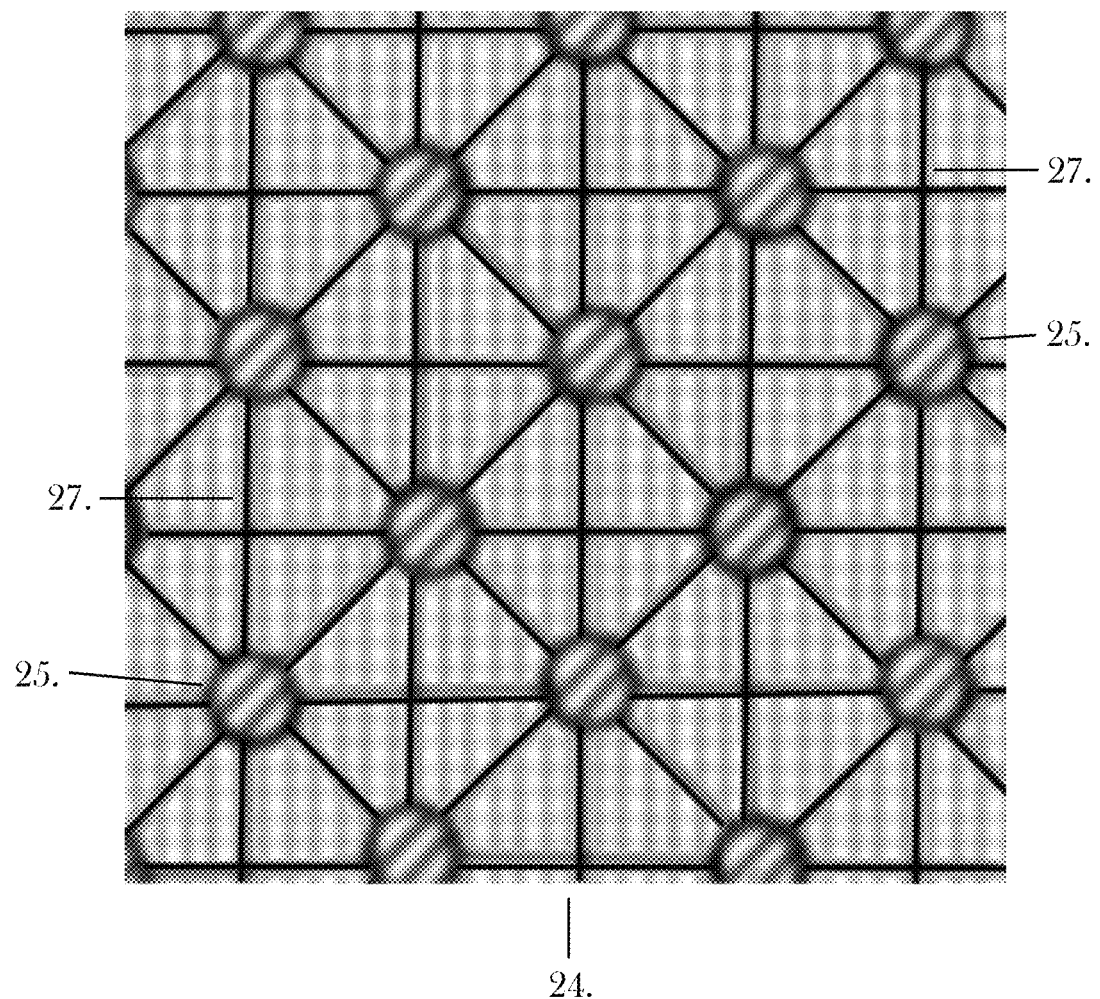

FIG. 22, extreme close up of Sensors on the Device for males' front right cup.

Figure 23:
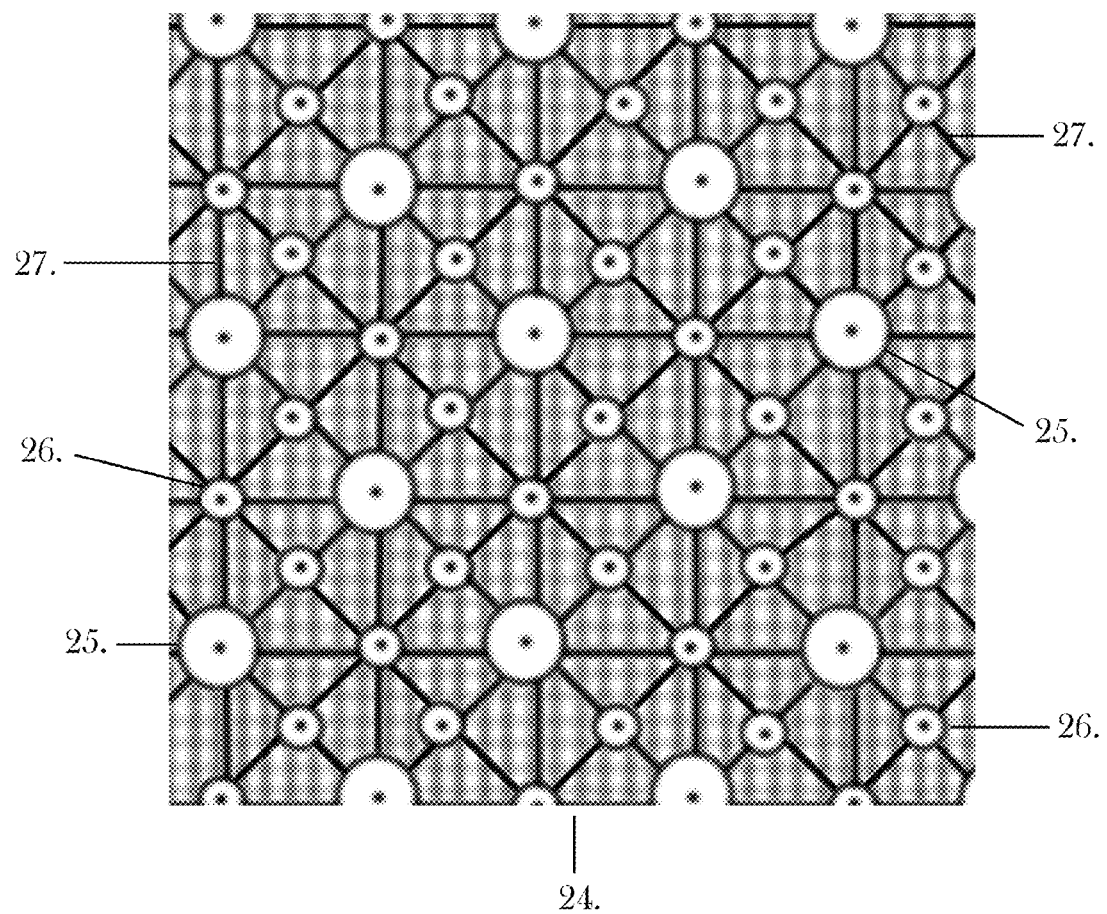

FIG. 23, extreme close up of Sensors on the Device for males' rear right cup.

Figure 24:
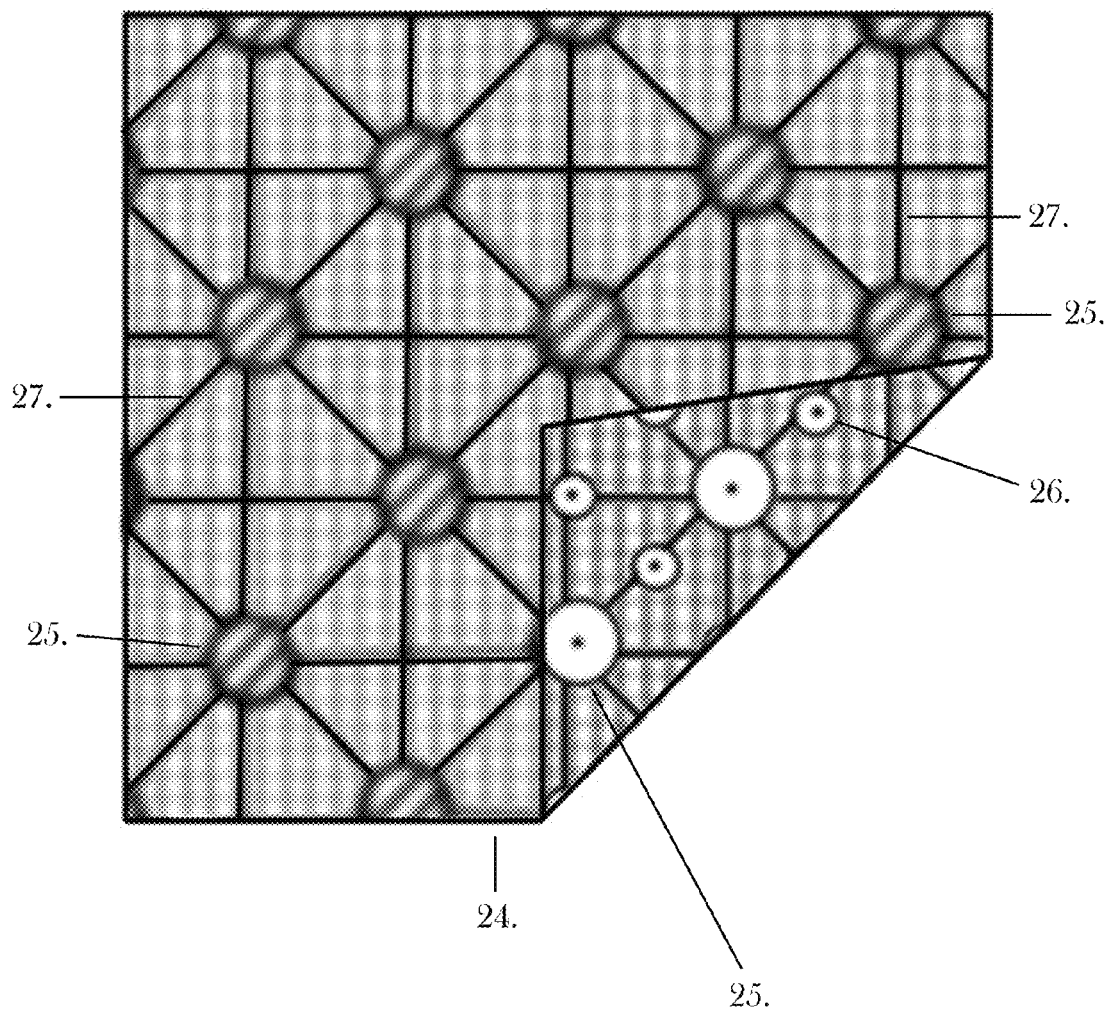

FIG. 24, extreme close up of Sensors on the Device for males' right cup, front and back.

Figure 25:
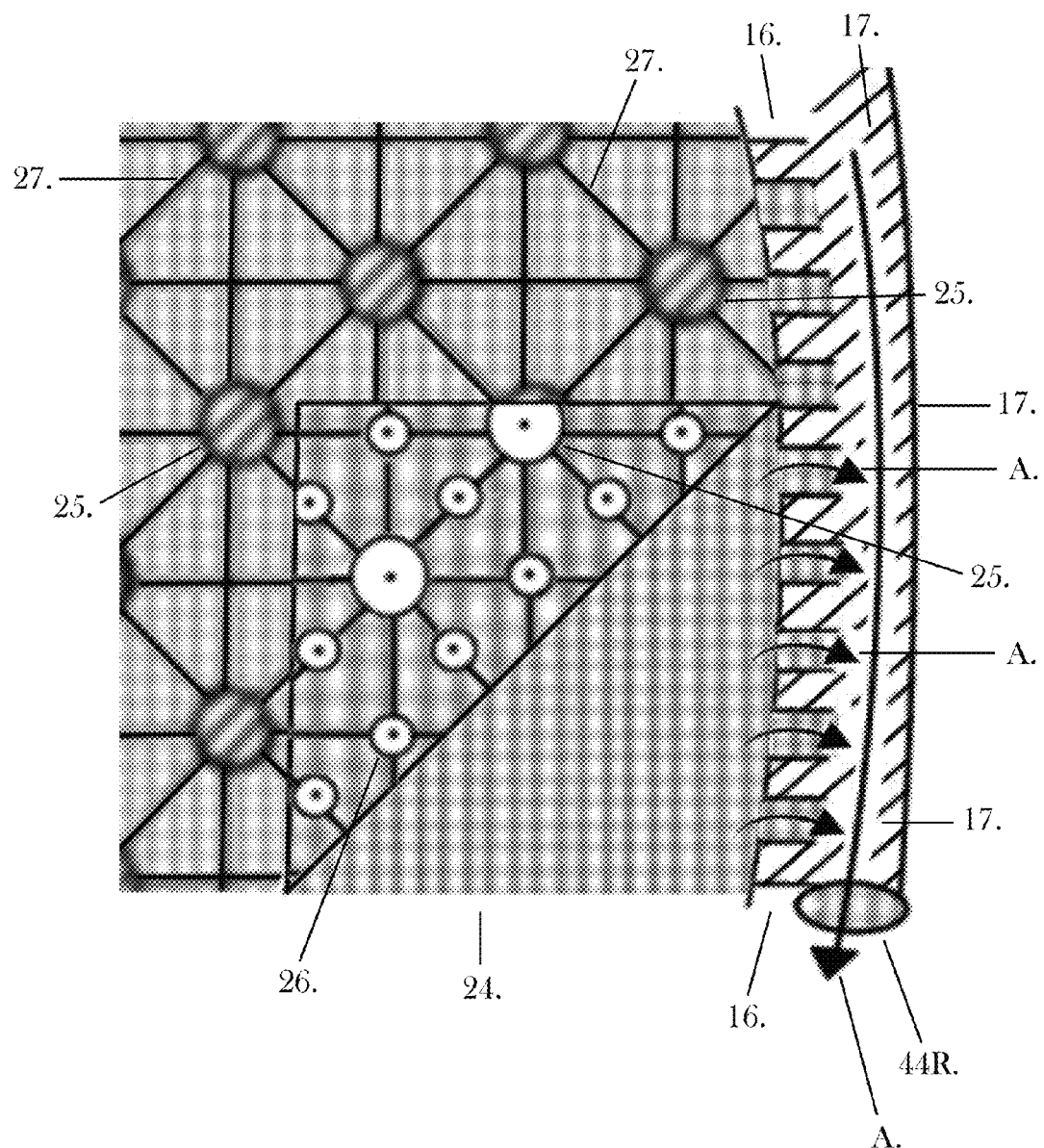

FIG. 25, extreme close up of Sensors on the Device for males' right cup, front and back, with Conforming Mesh and Vacuum Ability views.

Figure 26:
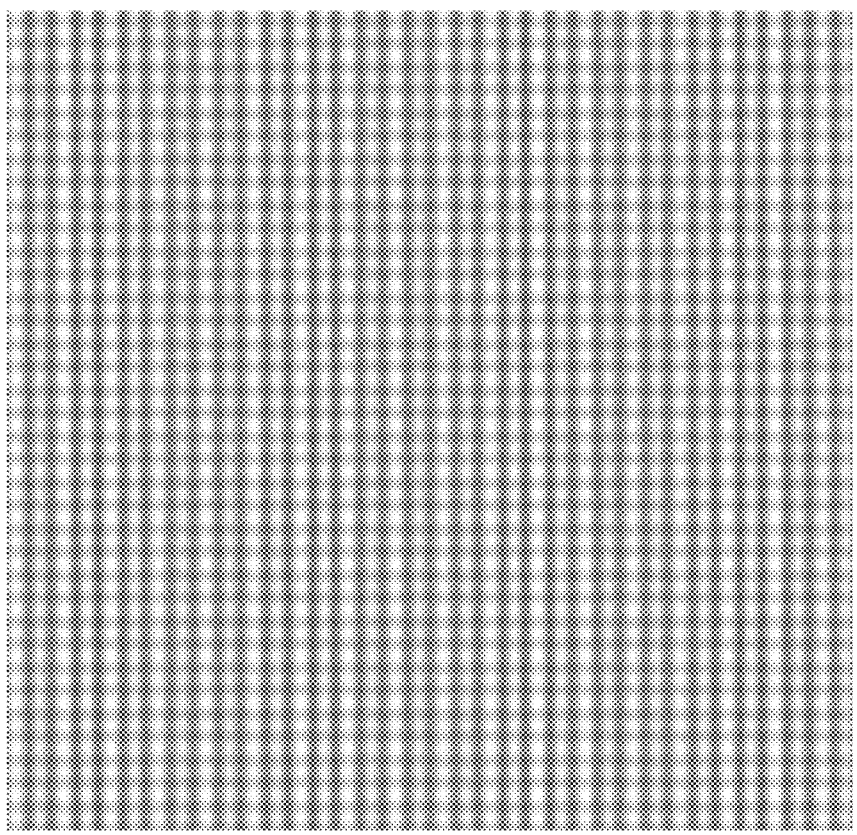

FIG. 26, close up of the Conforming Mesh.

FIG. 27, close up view of the Device for females, right rear section.

FIG. 27A, the Device for females' at right, rear.

FIG. 28, close up view of the Device for males, right rear section.

FIG. 28A, the Device for males' at right, rear.

Figure 29:
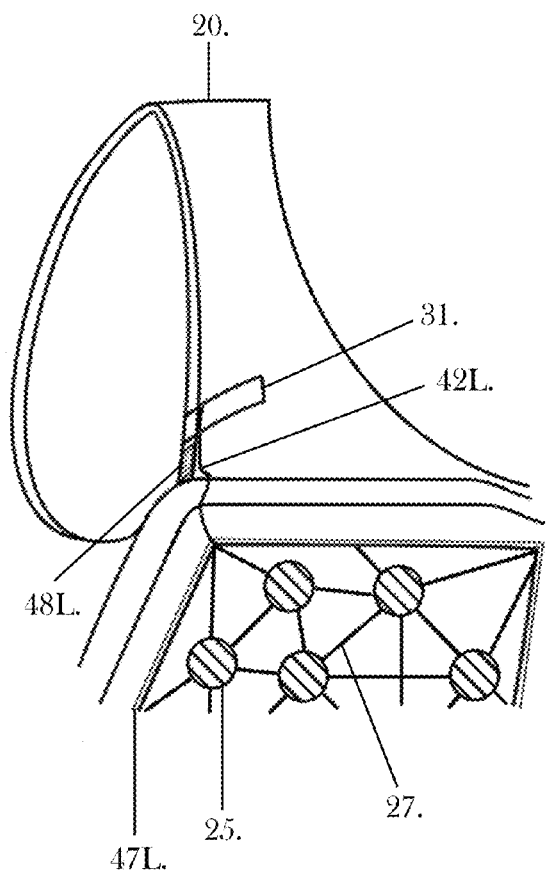

FIG. 29, the Device for males, extreme close up, right front, top.

Figure 29A:
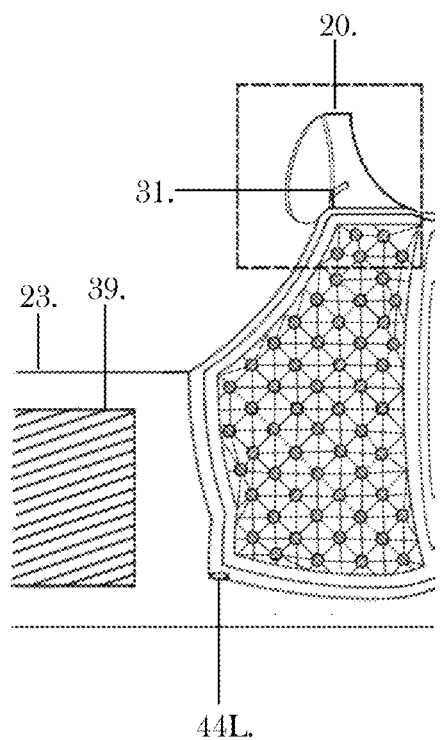

FIG. 29A, the Device for males, right front section.

Figure 30:
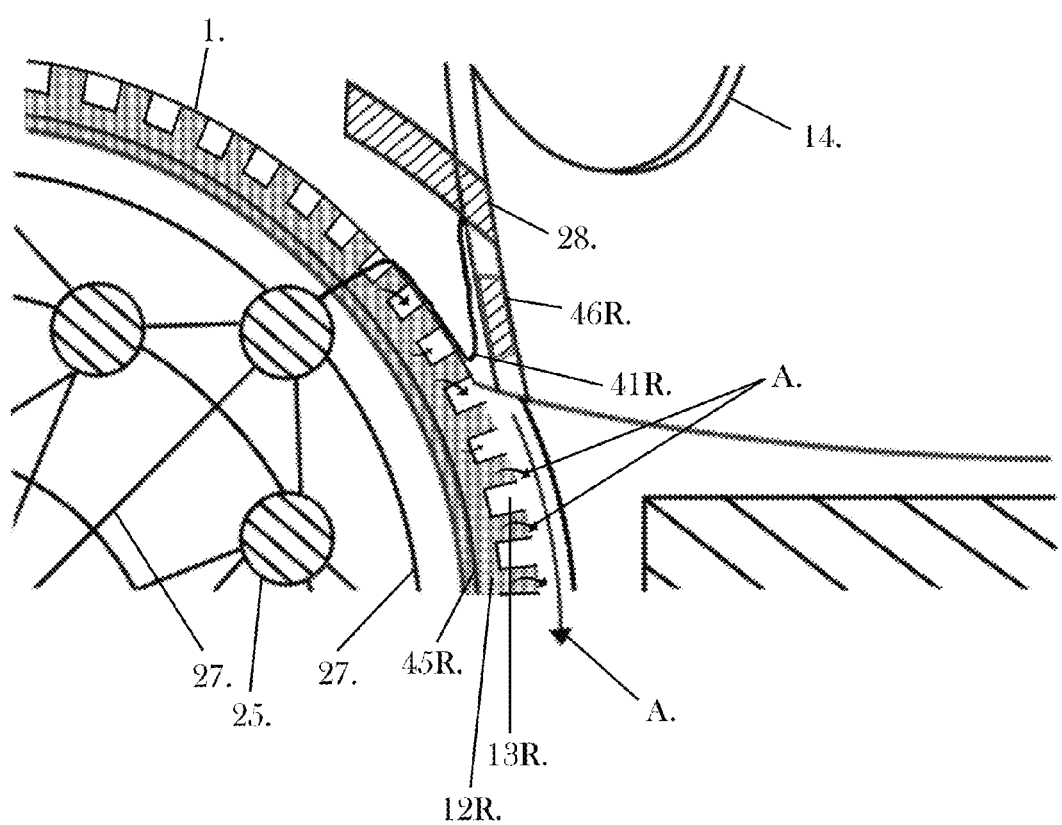

FIG. 30, the Device for females, extreme close up, upper left side.

FIG. 31, the Device for males, extreme close up, upper left side.

FIG. 31A, the Device for males, extreme close up, top left section.

DETAILED DESCRIPTION OF THE INVENTION

The Mammography Device for females, shown in FIG. 1 (FIG. 1 is suggested for the front page of this application), comes in three separate parts, one mold or cup for the right breast (as The Device is viewed on the pages of this Specification) (FIG. 1, Ref. 1), a second for the left breast (FIG. 1, Ref. 2), and a soft Secondary Torso Connector (FIG. 1, Ref. 3), which wraps around the patient helping to hold the instrument in place, when necessary. The separate parts allow different cup or mold sizes to be chosen in the case of, for example, a patient with a left breast that differs in size from her right one. Since The Device for females should be produced in varying cup sizes, so the patient or technician may choose each cup as if they were fitting a brassiere to the patient's individual breasts. The Device has a soft Sternum Connector (SC) and Sternum Connector Flap (SCF), FIG. 1, Ref. 4 and FIG. 1, Ref. 5, for female patients at the sternum. The Sternum Connector (SC) and Sternum Connector Flap (SCF) are both comprised of comfortable and soft material and as The Device is viewed from the front, the Sternum Connector Flap (SCF), which is connected to The Device on the right side, (FIG. 1, Ref. 5), should be placed through its Sternum Connector (SC), at the left, (FIG. 1, Ref. 4), as illustrated in FIG. 2A, where a close up is seen. In FIG. 2, the Device for females is shown open, or loose. The SCF permits the patient to adjust the instrument across her sternum. A male with gynecomastia may also use this Device, if deemed necessary; although it is hoped the Device for males will suit him well. The Device for males should be constructed of two parts and in considerably smaller to considerably larger sizes like its female counterpart, to accommodate either thinner or larger patients. The Device for male's molds or cups are also pliable to the patient's upper body for comfortable and thorough readings and has been conceived as one piece instead of two. See FIG. 6. The Device for males is pinched closer or more open at the patient's sternum with the fingers; it has no separate SC (Sternum Connector) or SCF (Sternum Connector Flap). Both The Device for females as well as the Device for males will have what is herein described as a Vacuum Ability (VA) or more simply, the "Ability". The Vacuum Ability is enabled by The Device's Vacuum Ports (VPs). The Vacuum Ability is first illustrated close up in FIG. 21 (for The Device for females) and allows both styles of The Device to quickly conform to a patient's breasts using suction at the Vacuum Ports (VPs) in FIG. 1, Ref. 43R and Ref. 43L for The Device for females and FIG. 6, Ref. 44R and Ref. 44L for The Device for males. In conjunction with The Device's Rim and Conforming Mesh, the Vacuum Ability will aid in The Device's operation for mammographs and in the ease of wearing of The Device. The Ability has openings called Vacuum Ports on the left and right cups or molds, on both The Device for females (FIG. 1, Ref. 43R and Ref. 43L) and The Device for males (FIG. 6, Ref. 44R and Ref. 44L) for a small vacuum hose to be inserted. Once the hose is inserted a quiet vacuum is created by turning on the suction. The Conforming Mesh then pulls itself into place around the breasts of the wearer and The Device's Rim is manipulated with the user's or a technician's fingers, if necessary, for a customized, painless fit.

The Mammography Device for Females

The Mammography Device for females, (called hereafter, The Device for females, or The Device), is a three piece Device. See FIG. 1. It comes with two breast "cups" or "molds", that are separable. Each cup is attached left breast cup to right breast cup, across the patient's sternum, with a soft, light weight and hypo-allergenic closure, called the Sternum Connector Flap (or SCF). The Sternum Connector Flap is made with hook and loop fasteners on its front side, see FIG. 2A. The SCF's right side is covered to its edges with loop fasteners (FIG. 2A, Ref. 36). The SCF's left side is covered to its edges with hook fasteners (FIG. 2A, Ref. 37).

Hook and loop fasteners are NOT illustrated on THE DEVICE in any place in this Application, rather, hatch marked shapes have been illustrated in their stead and reference lines used, to show their position on The Device.

The SCF is attached to the right breast cup (as The Device is viewed from the front). To connect the right breast cup to the left breast cup, the SCF is passed through the Sternum Connector (SC) on the left breast cup and folded back on itself, as shown in FIG. 2B. The Device should have a section of loop fasteners on its right Primary Torso Connector (PTC) (FIG. 1, Ref. 9), at the front, and a section of hook fasteners on its left PTC at the front, (FIG. 1, Ref. 10). The Device for females, as shown in rear view in FIG. 11, also should have loop fasteners on the right PTC (Primary Torso Connector) (FIG. 11, Ref. 11), at the reverse for patients that are able to close it around their torso without the aid of a Secondary Torso Connector (STC), (FIG. 1A, Ref. 3). In FIG. 12, The Device for females is shown from the rear closed, using only its left and right PTCs, without the aid of a an STC. The Device for females' STC's right side should be covered to its edges with hook fasteners (FIG. 1, Ref. 32). The Device for females' STC's left side should be covered to its edges with loop fasteners (FIG. 1, Ref. 33).

The Rim of The Device for females (FIG. 10), is also soft and pliable, made with a material that will facilitate The Device's transmitting of data to a computer or other computation machine. The Rim is comprised of two sections, the Inner Edge (FIG. 10A, Ref. 12L) and the Outer Edge (FIG. 10A, Ref. 13L). The Rim's pliability allows for the wearer to mold The Device to better conform to her body, in conjunction with the Vacuum Ability, illustrated in FIG. 21 and the Rim, in combination with The Device's Conforming Mesh, will allow the wearer to achieve a great fit, facilitating a more comfortable mammograph. The Rim's Outer Edge on The Device for females is along its circumference, at the most extreme parts of the cups or molds. The Outer Edge of The Rim is soft also and what the SC and SCF (Sternum Connector (FIG. 2A, Ref. 4) and Sternum Connector Flap (FIG. 2A, Ref. 5)) are attached to. In FIG. 21, The Device for females' Vacuum Ability is illustrated with arrows to show the direction of the flow of suction when the device is attached to a small vacuum hose at FIG. 21, Ref. 43R. Directions of suction airflow are labeled as FIG. 21, Ref. Arrows A.

Persons with variably sized breasts, (bilateral asymmetry) may pick from this product's various breast cup sizes, the one that best suits for a proper fit to her body. The patient should be confident that whatever cup size she picks, it will attach to its opposite "partner" with no issues because of the SC. For example, a female patient with a "d cup" measured size on her left breast and a "c cup" measured size on her right breast, may choose a left mold that is larger than a right mold. The two different breast cup sizes will attach over the patient's sternum with ease. If a single breast is to be examined, it may be feasible that one of The Device's cups or molds be used, for either a female or a male patient.

The Mammography Device for females has two soft "Horns" (FIG. 1, Refs. 14 and 15) which fit over the patient's shoulders for added support and comfort. Also available with The Device is the Secondary Torso Connector (STC) (FIG. 1, Ref. 3), which is a large, separate torso connector which allows The Device to be sized variably for larger patients and wraps around the individual's torso. For smaller patients, using the Primary Torso Connectors (PTCs) (FIG. 1, Ref. 6 and Ref. 7), without the use of the Secondary Torso Connector (STC) might be preferred. In FIG. 3A, The Device for females is shown empty and at its right side, with its movable right Horn in a static position (FIG. 3A, Ref. 14). FIG. 4A illustrates The Device for females empty and at its right side, with its right Horn in flexion, as an individual who might use The Device, may be able to manipulate it (FIG. 4A, Ref. 14). FIG. 5 depicts The Device for females empty and at its right side with a soft, large STC (Secondary Torso Connector) (FIG. 5, Ref. 3) attached to its soft, right PTC (Primary Torso Connector) (FIG. 5, Ref. 6).

The Mammography Device for Males

The Mammography Device for males, (called hereafter The Device for males, or The Device), will afford the male patient the same comfort and ease of use as its counterpart for females. The Device for males, (FIG. 6) is intended to be constructed in a variety of sizes and also intended to be constructed of the same materials as The Device for females; however; the design of The Device for males differs according to the presumptive differences in the basic physiology of male and female patients. It has a soft and pliable Rim along its Inner Edge, (FIG. 13A, Ref. 16), that a patient or technician can shape with fingers, to gently mold The Device along the patient's pectoralis major and the serratus anterior. This should insure exact coverage and a complete reading of the patient's breast matter.

In FIG. 7A, The Device for males is shown empty and at its right side, with its movable right Horn in a static position (FIG. 7A, Ref. 19). FIG. 8A illustrates The Device for males empty and at its right side, with its right Horn in flexion, as an individual who might use The Device, may be able to manipulate it (FIG. 8A, Ref. 19). FIG. 9 illustrates The Device for males empty and at its right side with a soft, large STC (Secondary Torso Connector) (FIG. 9, Ref. 18) attached to its soft, right PTC (Primary Torso Connector) (FIG. 9, Ref. 21).

The Device for males is a two piece device, connected to a patient's torso over his shoulders with soft Horns (FIG. 6, Ref. 19 and Ref. 20), like The Device for females. The Device should have a section of loop fasteners on its right Primary Torso Connector (PTC) (FIG. 6, Ref. 38), at the front, and a section of hook fasteners on its left PTC at the front, (FIG. 6, Ref. 39). The Device for males uses a STC (Secondary Torso Connector) (FIG. 6A, Ref. 18), to surround the anterior of the patient and connect The Device's left and right sides, if necessary. The Device, as shown in rear view in FIG. 15, also should have loop fasteners on its right PTC (Primary Torso Connector) (FIG. 15, Ref. 22), at the reverse for patients that are able to close it around their torso without the aid of a Secondary Torso Connector (STC) (FIG. 6, Ref. 18). In FIG. 16, The Device for males is shown from the rear closed, using only its left and right PTCs, without the aid of a STC. The Device for males' STC's right side (front) should be covered to its edges with hook fasteners (FIG. 6, Ref. 34). The Device for males' STC's left side (front) should be covered to its edges with loop fasteners (FIG. 6, Ref. 35). FIG. 17 depicts two of The Device for males' STC's, daisy chained. The properties, look and function of the STC for The Device for females and the STC for The Device for males, are equal. This means of connecting The Device to a patient's body is universal: The Device's Horns rest on a person's shoulder blades and a soft wide, STC fits around a patient, if needed, and the STC connects to The Device on left and right with a wide strip of hook and loop fasteners. The Device for males will be a two piece unit, not a three piece unit like the female counterpart. The Device for males' Rim will have a slight opening at the male patient's sternum, (FIG. 13, Ref. 40) with its Outer Edge outlining it, so that patients and or technicians, can mold the instrument for a more customized fit, to the patient's frame, which will assist The Device for males in its Vacuum Ability, as illustrated in FIG. 25. In FIG. 25, The Device for males' Vacuum Ability is illustrated with arrows to show the direction of the flow of suction when the device is attached to a small vacuum hose at FIG. 25, Ref. 44R. Directions of suction airflow are labeled as FIG. 25, Ref. Arrows A.

The Primary Torso Connectors and the Secondary Torso Connectors (and their Relationship to the RIM)

(Please note that the illustrations in this Application are not to scale.) The Device's Primary Torso Connectors (PTCs), on The Device for females as well as The Device for males, should be made from a soft hypo-allergenic, moisture resistant material, soft to the touch, but able to be wiped clean with a sanitizing wipe, if The Device has not been manufactured to be disposable. The PTCs are attached to the Rim of The Device (on both The Device for females as well as The Device for males), via the Rim's Outer Edge, so that there are no gaps or holes in between the PTCs and the Rim's Outer Edge and no gaps or holes in between the PTCs and The Device. See for The Device for females, FIG. 5, Ref. 6 and FIG. 5, Ref. 13R. For The Device for males, see FIG. 14A, Ref. 21 and FIG. 14A, Ref. 17. (FIG. 14 is a close up of The Device for males' left side and FIG. 14, Ref. 23 shows The Device for males' left Primary Torso Connector, while FIG. 14, Ref. 17, The Device for males' Rim's Outer Edge, with no holes or gaps in between the two.) The user of The Device should be able to pinch or push the Rim material against his or her skin and still get the best fit possible which will assist The Device in its Vacuum Ability, (as illustrated in FIG. 21, Ref. Arrows A), without affecting the PTCs integrity or ability to hold The Device onto the user's body. FIG. 21, Ref. Arrows A demonstrate the direction that airflow takes during suction. The Device's STCs (Secondary Torso Connectors) are made with the same material as The Device's PTCs and are attached to nothing, unless needed to extend The Device around the torso of a patient who is larger. The Device's STCs may be daisy chained, so that the larger patient who needs multiple STCs can comfortably fit The Device around his or her back. FIG. 17 illustrates the front view of one STC for males (FIG. 17, Ref. 18.1) connected via hook and loop fasteners, to another STC in rear view (FIG. 17, Ref. 18.2), for a daisy chain effect. FIG. 17, Ref. 34.1 illustrates The Device for males' Secondary Torso Connector's (STC's) RIGHT FRONT side, covered to its edges with hook fasteners, while FIG. 17, Ref. 35.1 depicts The Device's STC's LEFT FRONT side, covered to its edges with loop fasteners. FIG. 17, Ref. 34.2 is The Device for males' STCs at the RIGHT SIDE AT REAR, covered to its edges with hook fasteners and lastly, FIG. 17, Ref. 35.2 is The Device for males' STC at the LEFT SIDE AT REAR, covered to its edges with loop fasteners.

Using this example, the STCs could then be attached to The Device for males' PTCs (FIG. 6, Ref. 38 and Ref. 39) and fit comfortably around a larger patient, using care not to allow any hook fasteners to come in contact with a patient's skin (simply cover any hook fasteners with corresponding loop fasteners and use as many STCs as necessary to accomplish your task). The properties, look and function of the STCs for The Device for males, as well as the STCs for The Device for females, ARE EQUAL.

The Rim

The Rim has two sections that follow the entire mold or cup edges of The Device for both males and females. The two sections of The Rim are called the Inner Edge and the Outer Edge. See FIGS. 10 and 10A, Ref. 12L, Inner Edge for The Device for females and FIGS. 10 and 10A, Ref. 13L, Outer Edges for The Device for females. See FIGS. 14 and 14A Ref. 16, the Inner Edge for The Device for males and FIGS. 14 and 14A, Ref. 17, The Outer Edge for The Device for males. The Inner Edge as well as the Outer Edge on both The Device for males and The Device for females, are to be constructed with a hypo-allergenic material that is kept sterile with a sanitizing cloth wipe, unless The Device has been manufactured to be disposable. As previously stated, The Rim is flexible, which will assist in The Device's Vacuum Ability, as illustrated in FIG. 21. The Rim is meant to snugly conform to the torso along the breast; at the pectoralis major and the serratus anterior on the outsides of the chest and along the sternum (center of the chest), in The Device for males' design. This will allow the instrument's Sensors, to signal, or read, through all of a patient's breast tissue. The Rim may or may not have visible striations. The striations illustrated in this document on The Rims of the Device for females or males are to help the reader visualize the possibility of flexion in the instrument.

The Horns

The Device is attached to the torso not only by the PTCs and the STCs which may wrap the circumference of the patient from the sides to the back, but by two distinct rises out of The Device at the right top and left top, called Horns, because of their likeness to the horn of an animal when viewed from the side. The Horns are found on both The Device for females as well as The Device for males. The Horns themselves are also soft, as any part of The Device that comes in contact with human flesh is meant to be as positive and calming as possible for a patient. The Horns are meant to have enough flexion to move up or down and then farther from, or closer to, a patient's torso. When put in place, however, the Horns should stay firmly, but comfortably. The Horns will help to provide a comfortable means of additional stability for holding The Device in place. See FIG. 1, Ref. 14 and Ref. 15 and FIG. 6, Ref. 19 and Ref. 20.

The Conforming Mesh

The Device's cups or molds, for both females and males, are made of a Conforming Mesh (CM), hereafter called the Mesh, for brevity's sake. The Mesh may have opacity when it is viewed from the front. FIG. 18 is a conception of a close up of the FRONT side of the FRONT panel of the Conforming Mesh, illustrated in the style of The Device for females. FIG. 19 is a conception of a close up of the REAR side of the FRONT panel of the Conforming Mesh (CM), illustrated in the style of The Device for females. In FIG. 20, the front and rear views of the FRONT PANEL have been merged with the REAR PANEL to create the entire Mesh and are seen as they would be on The Device; however; in FIG. 21, The Vacuum Port (VP) at Ref. 43R, which enables The Device's Vacuum Ability, has been added in between the two layers. The Device for females has two Vacuum Ports that enable the Vacuum Ability through the Conforming Mesh. The Vacuum Ports for The Device for females are first seen in FIG. 1 at Ref. Arrows 43R and 43L. FIG. 21 shows the direction of the flow of suction, at Reference Arrows A, when The Device is attached to a small vacuum hose at its Vacuum Ports. FIG. 27 is a close up of the Mesh at the Device for females' left cup, rear view. FIG. 22 is a conception of a close up of FRONT side of the FRONT panel of the Conforming Mesh, illustrated in the style of The Device for males. FIG. 23 is a conception of a close up of the REAR side of the FRONT panel of the Conforming Mesh (CM), illustrated in the style of The Device for males. In FIG. 24, the front and rear views of the FRONT PANEL have been merged with the REAR PANEL to create the entire Mesh and are seen as they would be on The Device; however; in FIG. 25, The Vacuum Port (VP) at Ref. 44R, which enables The Device's Vacuum Ability, has been added in between the two layers. The Device for males has two Vacuum Ports that enable the Vacuum Ability through the Conforming Mesh. The Vacuum Ports for The Device for males are first seen in FIG. 6 at Refs. 44R and 44L. FIG. 25 shows the direction of the flow of suction, at Reference Arrows A, when The Device is attached to a small vacuum hose at its Vacuum Ports. FIG. 28 is a close up of the Mesh at The Device for males' left rear view. The Mesh should have a smooth, stretching quality, the smoothness because it will touch human flesh and the stretch quality to help it conform to the human figure. The Mesh should be constructed in a way that permits it to, with the suction built into it via the Vacuum Ability, be conformed through The Device's Rim around the breast and chest of a patient using either The Device for females or The Device for males. FIG. 21 is a depiction of a close up of the FRONT and BACK sides on the FRONT PANEL of the Conforming Mesh, merged together on the Device for females at the right cup. FIG. 25 is a depiction of a close up of FRONT and BACK sides on the FRONT PANEL of the Conforming Mesh, merged together on The Device for males at the right mold side. FIG. 26 is an illustration of the Mesh's REAR panel, which looks the same in both The Device for females as well as for males ALL VIEWS OF THE CONFORMING MESH (CM) HAVE BEEN CALLED REFERENCE 24 (for simplicity) AND IN ALL ILLUSTRATIONS OF THE CM IN THIS APPLICATION, A GRID-LIKE OR SCREEN-LIKE QUALITY HAS BEEN USED FOR ARTISTIC PURPOSES; THE DEVICE'S CONFORMING MESH SHOULD HAVE NO HOLES The Mesh is what the Vacuum Ability operates through and what the Sensors are attached to and facilitates The Device's ability to comfortably encompass, with the suction of the Vacuum Ability, a person's breasts and read through the breast matter, along with The Rim. The Conforming Mesh may be made of a lightweight and soft material that is conducive to a successful and clear first reading of the patient's physiology. The Conforming Mesh should be made of a material or materials that might consist of cloth, paper, a polymer or metallic or optical fibers, or any necessary combination of materials, that will give The Device its ability to not only fit an individual, but also to take an accurate breast tissue reading. The Vacuum Ability will draw the CM up snugly around a patient's breasts without tightness.

The Sensors

The Device's Sensors, as mentioned previously, accomplish the reading of the patient's breast matter. The Sensors are attached to the Conforming Mesh (CM), see FIG. 18, Ref. 25 and FIG. 19, Ref. 25 and Ref. 26 for The Device for females and FIG. 22, Ref. 25 and FIG. 23, Ref. 25 and Ref. 26 for The Device for males. FIG. 26 is a depiction of a close up of the Mesh at its rear panel, for both styles of The Device, with no Sensors or Mesh Lines. There are many Sensors on the Conforming Mesh, in two sizes, a large Sensor, FIG. 19, Refs. 25 and a small Sensor, FIG. 19, Refs. 26 (as illustrated for The Device for females) and FIG. 23, Refs. 25, along with FIG. 23, Refs. 26 (as illustrated for The Device for males). For the purposes of simplicity and ease of reference in this Application, large and small Sensors on either The Device for females or The Device for males, The Device's Mesh Lines and the Conforming Mesh itself, have been given the same reference numbers. There are too many Sensors and Mesh Lines to number practically for this Application. Small Sensors are not illustrated as seen from the front view of the Conforming Mesh. As should be expected, this Application uses artist's conceptions of the Sensors, as well as other technical aspects of The Device. The exact number and configuration of the large and small Sensors on The Device for females or The Device for males will not be known until The Device reaches production stages. Note: Sensors are not intended to be "cut", "split" or truncated, but may appear so in the drawings in this Application. The drawings in this Application are intended for descriptive purposes. The large and small Sensors are connected to one another with Mesh Lines (ML), as illustrated for The Device for females in FIG. 18, Refs. 27, FIG. 19, Refs. 27 and FIG. 20, Refs. 27 and as illustrated for The Device for males in FIG. 22, Refs. 27, FIG. 23, Refs. 27 and FIG. 24, Refs. 27. The Mesh Lines are connected to The Device's Rim, for both The Device for males and The Device for females. The Mesh Line Lead (MLL), (easily seen in FIG. 30 at Ref. 45R on The Device for females and FIG. 31, Ref. 47R on The Device for males), simply stated, runs the circumference of both the cups or molds on both styles of The Device, connecting the Grounding Point Wire (GPW) to the Mesh Lines, should data need to be transferred in that manner. A close up for the GPW on The Device for females is seen at FIG. 30 Ref. 41R and a close up for the GPW on The Device for males is seen at FIG. 31A Ref. 42R. The Sensors cover the Conforming Mesh's surface area and along with the Mesh Lines, facilitate complete readings of a patient's breast matter. The Sensors send and or receive signals through the breast tissue, to a computer or computation machine, operated by a medical technician or doctor. The Sensors will be able to read through breast tissue using the best method available, whether electromagnetic fields, light or auditory waves, nanotechnology, etc., and will create and send a 2 or 3 D image of the patient's breasts, to a computer or computation machine, allowing a doctor to view and interpret clinical findings. The Mammography Device may use or combine various technology and techniques, most notably those used in neuropsychology, X-ray computed tomography, and sonography. A reading, or 2 or 3 D image of the left and right breasts is taken when The Device's operator activates The Device from his or her computer or computation station. The Sensors will each have a specific identifiable placement in The Device's design, whether for females or males. For example, "L1, FSensor" may represent the number one sensor on the left side of a female patient's torso, or "R5, MSensor" may represent the number five sensor on the right side of a male patient's torso, to signify Sensor placement in The Device. This may enable ease in maintenance, or reading of findings by a doctor or technician. The prior example has NOT been illustrated in this Application. Individual Sensors may be able to be replaced in this case, if some malfunction is discovered. Both breasts are "read" simultaneously, allowing for a fast, complete and comfortable medical appointment. Results can be seen immediately or sent to a physician for interpretation. Either The Device for females or The Device for males may be ground for electricity via Grounding Points (GPs) at its right or left Horns, noted first in this Application for The Device for females in FIG. 1, at Ref. 28 and Ref. 29, and FIG. 6, at Ref. 30 and Ref. 31 for The Device for males. The Grounding Point Wire (GPW), at FIG. 3, Ref. 41R on The Device for females (seen in close up at left rear in FIG. 27, Ref. 41L on The Device for females) and FIG. 9, Ref. 42R on The Device for males (seen in close up at left front in FIG. 29, Ref. 42L on The Device for males), is an unobtrusive wire or cable running from The Device's Rims to the Grounding Points (GPs) on its Horns, on both the extreme left and extreme right sides of The Device for females, as well as The Device for males. The Grounding Point (GP) may be split into two small sections, one solely to ground The Device and if necessary, the other to aid it and The Grounding Point Wire (GPW) to be configured to transmit data from The Device to a computer, if the operator is not using wireless data transfer methods. The Device can also receive or transmit data from its USB (or data) ports, first seen in FIG. 3A, Ref. 46R for The Device for females (FIG. 30, Ref. 46R is a close up on The Device for females) and more easily seen on The Device for males in FIG. 31 at Ref. 48R. No left USB ports have been illustrated.

The Vacuum Ability

The Device's Vacuum Ability (VA), as illustrated in FIG. 21, Ref. A for The Device for females and FIG. 25, Ref. A for The Device for males, is facilitated by the Conforming Mesh (CM), as previously stated. It is intended that the CM be made from a material that is lightweight, upon OR inside of which the Mesh Lines and Sensors can ride, however; it should be without holes or perforations, except where it contacts The Device's Rim (facilitating suction) and where the Vacuum Ability's Vacuum Ports (VPs) rest. The Vacuum Ports for the Vacuum Ability should be at the lower aspects of the Rim on the left and right sides of both styles of The Device. With a light suction applied through the Ability's Vacuum Ports (first noted for The Device for females in FIG. 1, Refs. 43R and 43L and first noted for The Device for males in FIG. 6, Refs. 44R and 44L), The Device's Conforming Mesh will pull around and encompass the breasts of the wearer, enabling the Sensors and Mesh Lines to send and or receive information obtained about the wearer's breast tissue wirelessly or via a single USB (or data) port (FIG. 30, Ref. 46R on The Device for females, FIG. 31 at Ref. 48R on The Device for males), to a computer or computation machine for a physician's interpretation. FIG. 21 is a close up depiction of the Vacuum Ability in action, in The Device styled for females. Ref. A show the direction of a flow of suction out of the Vacuum Port at FIG. 21, Ref. 43R, attached to the Conforming Mesh in The Device styled for females, at the right cup or mold. The flexible Rim allows the vacuum flow through its Inner Edge at FIG. 21 Ref. 12R and to its Outer Edge at FIG. 21 Ref. 13R. Likewise, FIG. 25 is a close up depiction of the Vacuum Ability in action, in The Device styled for males. Ref. A show the direction of a flow of suction out of the Vacuum Port at FIG. 25, Ref. 44R, attached to the Conforming Mesh in The Device for males at the right cup or mold. The flexible Rim allows the vacuum flow through its Inner Edge at FIG. 25, Ref. 16 to its Outer Edge at FIG. 25 Ref. 17.

The Device will deliver results in quadrants, allowing for an exact location of suspect tissue, if suspect tissue exists, which might make surgery, if necessary, much more accurate and less "exploratory". Persons with spherical or conical, inverted, longer, or larger sized mammary papillae (nipples) may also comfortably use The Device.

DRAWINGS (Left and right views of the Drawings are described as seen on the Drawing Sheets and NOT as a person wearing The Device would see them, and are so labeled, except where indicated otherwise.)

(FIG. 1): Mammography Device for females, front view, with an accompanying Secondary Torso Connector (STC).

(FIG. 1, Ref. 1): The front view of The Mammography Device for females', right mold, or cup.

(FIG. 1, Ref. 2): The front view of The Mammography Device for females', left mold, or cup.

(FIG. 1A, Ref. 3): The front view of The Device for females', Secondary Torso Connector (or STC). The STC illustration, just as all of the illustrations contained herein, are not to scale.

(FIG. 1, Ref. 4): The front view of The Device for females', soft Sternum Connector (SC).

(FIG. 1, Ref. 5): Device for females' soft Sternum Connector Flap (SCF).

(FIG. 1, Ref. 4): The front view of The Mammography Device for females', soft Sternum Connector (SC).

(FIG. 2): The front view of The Device for females, shown open, or loose.

(FIG. 2B): The front view of The Device for females, shown closed, or fastened, by The Device's Sternum Connector Flap (SCF).

(FIG. 6): The Device for males, front view, with an accompanying Secondary Torso Connector (STC).

(FIG. 21): An illustrated section of The Device for females' Conforming Mesh (CM). This illustration also depicts the CM's Vacuum Ability and the right Vacuum Port of The Device for females. Reference Arrows "A" indicate the proposed direction of suction in between the front and rear sections of the CM, that the Vacuum Ability takes through The Device's Rim and out of the right Vacuum Port.

(FIG. 1, Ref. 43R): The Device for females' right Vacuum Port (which facilitates its Vacuum Ability), connected to the Conforming Mesh on The Device for females' right Rim.

(FIG. 1, Ref. 43L): The Device for females' left Vacuum Port (which facilitates its Vacuum Ability), connected to the Conforming Mesh on The Device for females' left Rim.

(FIG. 6, Ref. 44R): The Device for males' right Vacuum Port (which facilitates its Vacuum Ability), connected to the Conforming Mesh on The Device for males' Rim at the right side.

(FIG. 6, Ref. 44L): The Device for males' left Vacuum Port (which facilitates its Vacuum Ability), connected to the Conforming Mesh on The Device for males' Rim at the left side.

(FIG. 1, Ref. 43R): The Device for females' right Vacuum Port (which facilitates its Vacuum Ability), connected to the Conforming Mesh on The Device for females' right Rim.

(FIG. 1, Ref. 43L): The Device for females' left Vacuum Port (which facilitates its Vacuum Ability), connected to the Conforming Mesh on The Device for females' left Rim.

(FIG. 6, Ref. 44R): The Device for males' right Vacuum Port (which facilitates its Vacuum Ability), connected to the Conforming Mesh on The Device for males' Rim at the right side.

(FIG. 6, Ref. 44L): The Device for males' left Vacuum Port (which facilitates its Vacuum Ability), connected to the Conforming Mesh on Device for males' Rim at the left side.

(FIG. 1): The Device for females', front view, with an accompanying Secondary Torso Connector (STC) at FIG. 1A.

(FIG. 2): The front view of The Device for females, shown open at The Device's Sternum Connector Flap (SCF).

(FIG. 2A, Ref. 36): The RIGHT front side view of The Device for females', Sternum Connector Flap (SCF), covered to its edges with loop fasteners.

(FIG. 2A, Ref. 37): The LEFT front side view of The Device for females' Sternum Connector Flap (SCF), covered to its edges with hook fasteners.

(FIG. 2): The front view of The Device for females, shown closed, or fastened, at The Device's Sternum Connector Flap (SCF).

(FIG. 1, Ref. 9): The front view of The Device for females' RIGHT Primary Torso Connector (PTC) with a section of loop fasteners attached. The PTCs have been foreshortened to fit the page; the illustrations in this application are not to scale.

(FIG. 1, Ref. 10): The front view of The Device for females' LEFT Primary Torso Connector (PTC) with a section of hook fasteners attached.

(FIG. 11): The Device for females, rear view, with an accompanying Secondary Torso Connector (STC, rear view).

(FIG. 11, Ref. 11): The Device for females, rear view, with "loop" fasteners on the right rear Primary Torso Connector (PTC).

(FIG. 1A, Ref. 3): The front view of The Device for females' soft Secondary Torso Connector (STC).

(FIG. 12): The rear view of The Device for females' soft right and left Primary Torso Connectors (PTCs), when fastened. In this depiction, the soft Secondary Torso Connector (STC) has not been used.

(FIG. 1A, Ref. 32): The Device for females' Secondary Torso Connector's (STC's) right side, covered to its edges with hook fasteners.

(FIG. 1A, Ref. 33): The Device for females' Secondary Torso Connector's (STC's) left side, covered to its edges with loop fasteners.

(FIG. 10): The front view close up of The Device for females' Rim, at the left.

(FIG. 10, Ref. 12L): The front view close up of The Device for females', Rim's Inner Edge.

(FIG. 10, Ref. 13L): The front view close up of The Device for females' Rim's Outer Edge.

(FIG. 21): An illustrated section of The Device for females' Conforming Mesh (CM). This illustration also depicts the CM's Vacuum Ability and the right Vacuum Port of The Device for females. Reference Arrows "A" indicate the proposed direction of suction in between the front and rear sections of the CM, that the Vacuum Ability takes through The Device's Rim and out of the right Vacuum Port.

(FIG. 2A, Ref. 4): The front view of The Device for females' Sternum Connector (SC).

(FIG. 2A, Ref. 5): The front view of The Device for females' Sternum Connector Flap (SCF).

(FIG. 21): An illustrated section of The Device for females' Conforming Mesh (CM). This illustration also depicts the CM's Vacuum Ability and the right Vacuum Port of The Device for females. Reference Arrows "A" indicate the proposed direction of suction in between the front and rear sections of the CM, that the Vacuum Ability takes on its way through The Device's Rim and out of the right Vacuum Port.

(FIG. 21, Ref. 43R): An illustration of The Device for females' right Vacuum Port (VP) on the Conforming Mesh (CM).

(FIG. 21, Ref. A): An illustration of The Vacuum Ability's suction occurring through the Conforming Mesh at The Device for females' right Vacuum Port.

(FIG. 1, Ref. 14): The front view of The Device for females' flexible right Horn.

(FIG. 1, Ref. 15): The front view of The Device for females' flexible left Horn.

(FIG. 1A, Ref. 3): The front view of The Device for females' soft Secondary Torso Connector (STC).

(FIG. 1, Ref. 6): The front view of The Device for females' soft right Primary Torso Connector (PTC).

(FIG. 1, Ref. 7): The front view of The Device for females' soft left Primary Torso Connector (PTC).

(FIG. 3): The Device for females, empty and viewed at its front right section and its right side.

(FIG. 3A, Ref. 14): The Device for females, empty and viewed at its front right section and its right side, with its movable right Horn in a static position.

(FIG. 4): The Device for females, empty and viewed at its front right section and its right side.

(FIG. 4A, Ref. 14): The Device for females, empty and viewed at its front right section and its right side, with its right Horn in flexion.

(FIG. 4): The Device for females, empty and at its right cup side (as The Device is viewed from the front).

(FIG. 5, Ref. 3): The Device for females, empty and at its right cup side with a soft, large STC (Secondary Torso Connector) attached.

(FIG. 5, Ref. 6): The Device for females, empty and at its right cup side, right PTC (Primary Torso Connector) attached to the STC.

(FIG. 6): The Device for males, front view, with an accompanying Secondary Torso Connector (STC) at FIG. 6A.

(FIG. 13, Ref. 16): The front view close up of The Device for males', Rim's Inner Edge.

(FIG. 7): The Mammography Device for males, empty and viewed at its front right section (as The Device is viewed from the front).

(FIG. 7A, Ref. 19): The Device for males, empty and viewed at its front right section and its right side, with its movable right Horn in a static position.

(FIG. 8): The Device for males, empty and viewed at its front right section.

(FIG. 8A, Ref. 19): The Device for males, empty and viewed at its front right section and its right side, with its right Horn in flexion.

(FIG. 9): The Device for males, empty and at its right cup side (as The Device is viewed from the front).

(FIG. 9, Ref. 18): The Device for males, empty and at its right cup side with a soft, large STC (Secondary Torso Connector) attached.

(FIG. 9, Ref. 21): The Device for males, empty and at its right cup side, right PTC (Primary Torso Connector) attached to the STC.

(FIG. 6, Ref. 19): The front view of The Device for males' flexible right Horn.

(FIG. 6, Ref. 20): The front view of The Device for males' flexible left Horn.

(FIG. 6, Ref. 38): The front view of The Device for males' RIGHT Primary Torso Connector (PTC) with a section of loop fasteners attached.

(FIG. 6, Ref. 39): The front view of The Device for males' LEFT Primary Torso Connector (PTC) with a section of hook fasteners attached.

(FIG. 6, Ref. 18): The front view of The Device for males' soft Secondary Torso Connector (STC).

(FIG. 15): The Device for males, rear view, with an accompanying Secondary Torso Connector (STC, rear view) at FIG. 15A.

(FIG. 15, Ref. 22): The Device for males, rear view, with "loop" fasteners on the right rear Primary Torso Connector (PTC).

(FIG. 6, Ref. 18): The front view of The Device for males' soft Secondary Torso Connector (STC).

(FIG. 16): The rear view of The Device for males' soft right and left Primary Torso Connectors (PTCs), when fastened. In this depiction, the soft Secondary Torso Connector (STC) has not been used.

(FIG. 6, Ref. 34). The Device for males' Secondary Torso Connector's (STC's) right side, covered to its edges with hook fasteners.

(FIG. 6, Ref. 35): The Device for males' Secondary Torso Connector's (STC's) left side, covered to its edges with loop fasteners.

(FIG. 17): Depiction of two of The Device for males' STCs, daisy chained. The properties, look and function of the STCs for The Device for males, as well as the STCs for The Device for females, are equal.

(FIG. 13, Ref. 40): The Device for males' slight opening, in its center, at a patient's sternum.

(FIG. 25): An illustrated section of The Device for males' Conforming Mesh (CM). This illustration also depicts the CM's Vacuum Ability and the right side Vacuum Port of The Device for males. Reference Arrows "A" indicate the proposed direction of suction in between the front and rear sections of the CM, that the Vacuum Ability takes on its way through The Device's Rim and out of its right side Vacuum Port.

(FIG. 25, Ref. 44R): An illustration of The Device for males' right side Vacuum Port (VP) on the Conforming Mesh (CM).

(FIG. 25, Ref. A): An illustration of The Vacuum Ability's suction occurring through the Conforming Mesh at The Device for males' right side Vacuum Port.

(FIG. 5, Ref. 6): The Device for females' right Primary Torso Connector (PTC) attached to its right cup, or mold. There are no gaps between The Device's right or left PTCs and its right or left cups or molds Rims' Outer Edges.

(FIG. 5, Ref. 13R): The Device for females' right Rim's Outer Edge attached to its right PTC. There are no gaps between The Device's Rims' Outer Edges at its right or left cups or molds and its right or left Primary Torso Connectors (PTCs).

(FIG. 9, Ref. 21): The Device for males' right Primary Torso Connector (PTC) attached to its right cup, or mold. There are no gaps between The Device's right or left PTCs and its right or left cups or molds Rims' Outer Edges.

(FIG. 9, Ref. 17): The Device for males' right Rim's Outer Edge attached to its right PTC. There are no gaps between The Device's Rims' Outer Edges at its right or left cups or molds and its right or left Primary Torso Connectors (PTCs).

(FIG. 14): A close up depiction of The Device for males' left side (when viewed from the front).

(FIG. 14, Ref. 23): The Device for males' left Primary Torso Connector (PTC), with no hole or gap between itself and the Outer Edge of the Rim.

(FIG. 14, Ref. 17): The Device for males', Rim's Outer Edge, with no hole or gap between itself and the left Primary Torso Connector (PTC).

(FIG. 25, Ref. A): An illustration of The Vacuum Ability's suction occurring through the Conforming Mesh at The Device for males' right side Vacuum Port.

(FIG. 17): Depiction of two of The Device's STCs, daisy chained. The properties, look and function of the STCs for The Device for males, as well as the STCs for The Device for females, are equal.

(FIG. 17, Ref. 18.1): A depiction of The Mammography Device for males', Secondary Torso Connector, front view, daisy chained with another "male" STC.

(FIG. 17, Ref. 18.2): A depiction of The Device for males', Secondary Torso Connector, rear view, daisy chained with another "male" STC.

(FIG. 17, Ref. 34.1). The Device for males' Secondary Torso Connector's (STC's) right front side, covered to its edges with hook fasteners.

(FIG. 17, Ref. 35.1): The Device for males' Secondary Torso Connector's (STC's) left front side, covered to its edges with loop fasteners.

(FIG. 17, Ref. 34.2). The Device for males' Secondary Torso Connector's (STC's) right side at rear, covered to its edges with hook fasteners.

(FIG. 17, Ref. 35.2): The Device for males' Secondary Torso Connector's (STC's) left side at rear, covered to its edges with loop fasteners.

(FIG. 6, Ref. 38): The Device for males' right Primary Torso Connector (PTC), as viewed from the front, covered to its edges with loop fasteners.

(FIG. 6, Ref. 39): The Device for males' left Primary Torso Connector (PTC), as viewed from the front, covered to its edges with hook fasteners.

(FIG. 2A, Ref. 12R): The Device for females' right Rim's Inner Edge.

(FIG. 2A, Ref. 12L): The Device for females' left Rim's Inner Edge.

(FIG. 2A, Ref. 13R): The Device for females' right Rim's Outer Edge.

(FIG. 2A, Ref. 13L): The Device for females' left Rim's Outer Edge.

(FIG. 13A, Ref. 16): The Device for males' Inner Edge at its right mold or cup.

(FIG. 13A, Ref. 17): The Device for males' Outer Edge at its left mold or cup.

(FIG. 25): An illustrated section of The Device for males' Conforming Mesh (CM). This illustration also depicts the CM's Vacuum Ability and the right side Vacuum Port of The Device for males. Reference Arrows "A" indicate the proposed direction of suction in between the front and rear sections of the CM, that the Vacuum Ability takes on its way through The Device's Rim and out of its right side Vacuum Port.

(FIG. 1, Ref. 14): The Device for females' soft and flexible right Horn.

(FIG. 1, Ref. 15): The Device for females' soft and flexible left Horn.

(FIG. 6, Ref. 19): The Device for males' soft and flexible right Horn.

(FIG. 6, Ref. 20): The Device for males' soft and flexible left Horn.

(FIG. 18): A depiction of a close up of a FRONT SIDE (right) of The Device for females' Conforming Mesh's FRONT panel.

(FIG. 19): A depiction of a close up of a front panel's REAR side on The Device for females' Conforming Mesh, at right.

(FIG. 20): A depiction of a close up of the front and rear sides of the front panel of the Conforming Mesh, merged together with its rear panel, on The Device for females at the right cup.

(FIG. 21, Ref. 43R): A depiction of the right Vacuum Port on The Device for females' Conforming Mesh.

(FIG. 1, Ref. 43R): The Device for females' right Vacuum Port (which facilitates its Vacuum Ability), connected to the Conforming Mesh on The Device for females' right Rim.

(FIG. 1, Ref. 43L): The Device for females' left Vacuum Port (which facilitates its Vacuum Ability), connected to the Conforming Mesh on The Device for females' left Rim.

(FIG. 21, Ref. A): An illustration of The Vacuum Ability's suction occurring through the Conforming Mesh at The Device for females' right Vacuum Port.
Reference Arrows "A" indicate the proposed direction of suction in between the front and rear panels of the CM, that the Vacuum Ability takes on its way through The Device's Rim and out of the right Vacuum Port.

(FIG. 19): A depiction of a close up of the Conforming Mesh (CM) at The Device for females' left rear view. Note:

Sensors are not intended to be "cut", "split" or truncated, but may appear so in the drawings in this Application. The drawings in this application are intended for descriptive purposes.

(FIG. 22): A depiction of a close up of a FRONT SIDE (right) of The Device for males' Conforming Mesh's FRONT panel.

(FIG. 23): A depiction of a close up of a front panel's REAR side on The Device for males' Conforming Mesh, at right.

(FIG. 24): A depiction of a close up of the front and rear sides of the front panel of the Conforming Mesh, merged together with its rear panel, on The Device for males at the right cup.

(FIG. 25, Ref. 44R): A depiction of the right Vacuum Port on The Device for males' Conforming Mesh.

(FIG. 6, Ref. 44R): The Device for males' right Vacuum Port (which facilitates its Vacuum Ability), connected to the Conforming Mesh on The Device for males' Rim at the right side.

(FIG. 6, Ref. 44L): The Device for males' left Vacuum Port (which facilitates its Vacuum Ability), connected to the Conforming Mesh on The Device for males' Rim at the left side.

(FIG. 25, Ref. A): An illustration of The Vacuum Ability's suction occurring through the Conforming Mesh at The Device for males' right side Vacuum Port.
Reference Arrows "A" indicate the proposed direction of suction in between the front and rear panels of the CM, that the Vacuum Ability takes on its way through The Device's Rim and out of the right Vacuum Port.

(FIG. 23): A close up of the Conforming Mesh (CM) at The Device for males' left rear view. Note: Sensors are not intended to be "cut", "split" or truncated. Drawings in this application are for descriptive purposes.

(FIG. 21): An illustrated section of The Device for females' Conforming Mesh (CM). This illustration also depicts the CM's Vacuum Ability and the right side Vacuum Port of The Device for females. Reference Arrows "A" indicate the proposed direction of suction in between the front and rear sections of the CM, that the Vacuum Ability takes on its way through The Device's Rim and out of its right side Vacuum Port.

(FIG. 25): An illustrated section of The Device for males' Conforming Mesh (CM). This illustration also depicts the CM's Vacuum Ability and the right side Vacuum Port of The Device for males. Reference Arrows "A" indicate the proposed direction of suction in between the front and rear sections of the CM, that the Vacuum Ability takes on its way through The Device's Rim and out of its right side Vacuum Port.

(FIG. 26): A depiction of a close up of the Conforming Mesh's REAR PANEL, which looks the same in both The Device for females and The Device for males. All views of the Conforming Mesh (CM) have been called "Ref. 24" (for simplicity) and in all illustrations of the CM in this application, a grid-like or screen-like quality has been used for artistic purposes; The Device's Conforming Mesh should have no holes.

(FIG. 18, Ref. 25): A depiction of a close up of the FRONT view of one of the Conforming Mesh's (CM's) LARGE Sensors. The exact number and configuration of the Sensors on The Device will not be known until The Device reaches production stages. This drawing intends to illustrate The Device for females' Sensors as shown.

(FIG. 19, Ref. 25): A depiction of a close up of the REAR view of one of the Conforming Mesh's (CM's) LARGE Sensors. The exact number and configuration of the Sensors on The Device will not be known until The Device reaches production stages. This drawing intends to illustrate The Device for females' Sensors at rear as shown.

(FIG. 19, Ref. 26): A depiction of a close up of the REAR view of one of the Conforming Mesh's (CM's) SMALL Sensors. The exact number and configuration of the Sensors on The Device will not be known until The Device reaches production stages. This drawing intends to illustrate The Device for females' Sensors as shown.

(FIG. 22, Ref. 25): A depiction of a close up of the FRONT view of one of the Conforming Mesh's (CM's) LARGE Sensors. The exact number and configuration of the Sensors on The Device will not be known until The Device reaches production stages. This drawing intends to illustrate The Device for males' Sensors as shown.

(FIG. 23, Ref. 25): A depiction of a close up of the REAR view of one of the Conforming Mesh's (CM's) LARGE Sensors. The exact number and configuration of the Sensors on The Device will not be known until The Device reaches production stages. This drawing intends to illustrate The Device for males' Sensors as shown.

(FIG. 23, Ref. 26): A depiction of a close up of the REAR view of one of the Conforming Mesh's (CM's) SMALL Sensors. The exact number and configuration of the Sensors on The Device will not be known until The Device reaches production stages. This drawing intends to illustrate The Device for males' Sensors as shown.

(FIG. 26): A depiction of a close up of the Conforming Mesh's REAR PANEL, which looks the same in both The Device for females and The Device for males, with no Sensors or Mesh Lines.

(FIG. 27, Ref. 25): A depiction of a close up of the rear view of one of the Conforming Mesh's large Sensors on The Device for females.

(FIG. 27, Ref. 26): A depiction of a close up of the rear view of one of the CM's small Sensors on The Device for females.

(FIG. 27A): A partial drawing of The Device for female's rear view, repeated for reference.

(FIG. 28, Ref. 25): A depiction of a close up of the rear view of one of the Conforming Mesh's large Sensors on The Device for males.

(FIG. 28, Ref. 26): A depiction of a close up of the rear view of one of the CM's small Sensors on The Device for males.

(FIG. 28A): A partial drawing of The Device for male's rear view, repeated for reference.

(FIG. 10, Ref. 27): A depiction of a close up of the front view of the Conforming Mesh's, Mesh Lines (ML) on The Device for females. The Mesh Lines connect The Device's large and small Sensors to one another and to The Device's Rim.

(FIG. 10A, Ref. 27): A depiction of a close up of the rear view of the Conforming Mesh's (CM's), Mesh Lines (ML) on The Device for females.

(FIG. 18, Ref. 27): Another depiction of a close up of the front view of the CM's, Mesh Lines (ML) on The Device for females.

(FIG. 22, Ref. 27): A depiction of a close up of the front view of the Conforming Mesh's, Mesh Lines (ML) on The Device for males. The Mesh Lines connect The Device's large and small Sensors to one another and to The Device's Rim.

(FIG. 23, Ref. 27): A depiction of a close up of the rear view of the Conforming Mesh's (CM's), Mesh Lines (ML) on The Device for males.

(FIG. 24, Ref. 27): Another depiction of a close up of the front view of the CM's, Mesh Lines (ML) on The Device for males.

(FIG. 30, Ref. 45R): The Device for females' Mesh Line Lead (MLL). The MLL runs the entire circumference of both cups or molds of The Device for females on both its right and left sides in between the CM and the Rim's Outer Edge, along the Rim's Inner Edge.

(FIG. 31, Ref. 47R): The Device for males' Mesh Line Lead (MLL). The MLL runs along the entire mold of The Device for males on both its right and left sides in between The Device's CM and the Rim's Outer Edge, along the Rim's Inner Edge.

(FIG. 1, Ref. 28): Grounding Point (GP) on The Device for females' right Horn.

(FIG. 1, Ref. 29): Grounding Point (GP) on The Device for females' left Horn.

(FIG. 6, Ref. 30): Grounding Point (GP) on The Device for males' right Horn.

(FIG. 6, Ref. 31): Grounding Point (GP) on The Device for males' left Horn.

(FIG. 3, Ref. 41R): Right side (as viewed from the front) of The Device for females', Grounding Point Wire (GPW).

(FIG. 27, Ref. 41L): Left side (as viewed from the front) REAR close up of The Device for females, Grounding Point Wire (GPW).

(FIG. 9, Ref. 42R): Right side (as viewed from the front) of The Device for males', Grounding Point Wire (GPW).

(FIG. 29, Ref. 42L): As viewed from the front, left side FRONT close up of The Device for males, Grounding Point Wire (GPW).

(FIG. 3A, Ref. 46R): The Device for females' right USB data port. The Device for females' left USB data port is not shown in this Application.

(FIG. 30, Ref. 46R): A close up of The Device for females' right USB data port. The Device for females' opposite side USB data port is not shown in this Application.

(FIG. 31A, Ref. 48R): A close up of The Device for males' right USB data port. The Device for males' left opposite side USB data port is not shown in this Application.

(FIG. 21, Ref. A): An illustration of The Vacuum Ability's suction occurring through the Conforming Mesh at The Device for females' right Vacuum Port.

(FIG. 25, Ref. A): An illustration of The Vacuum Ability's suction occurring through the Conforming Mesh at The Device for males' right Vacuum Port.

(FIG. 1, Ref. 43R): The Device for females' right Vacuum Port (which facilitates its Vacuum Ability), connected to the Conforming Mesh on The Device for females' right Rim.

(FIG. 1, Ref. 43L): The Device for females' left Vacuum Port (which facilitates its Vacuum Ability), connected to the Conforming Mesh on The Device for females' left Rim.

(FIG. 6, Ref. 44R): The Device for males' right Vacuum Port (which facilitates its Vacuum Ability), connected to the Conforming Mesh on The Device for males' Rim at the right side.

(FIG. 6, Ref. 44L): The Device for males' left Vacuum Port (which facilitates its Vacuum Ability), connected to the Conforming Mesh on The Device for males' Rim at the left side.

(FIG. 30, Ref. 46R): A close up of The Device for females' right USB data port. The Device for females' opposite side USB data port is not shown in this Application.

(FIG. 31, Ref. 48R): A close up of The Device for males' right USB data port. The Device for males' opposite side USB data port is not shown in this Application.

(FIG. 21, Ref. A): An illustration of The Vacuum Ability's suction occurring through the Conforming Mesh at The Device for females' right Vacuum Port.

(FIG. 21, Ref. 43R): An illustration of The Device for females' right Vacuum Port (VP) on the Conforming Mesh (CM).

(FIG. 21, Ref. 12R): The Device for females' right Rim's Inner Edge, in close up on the Conforming Mesh, allowing suction from the Vacuum Ability to flow through it and out, so that it may comfortably conform to a wearer's breast.

(FIG. 21, Ref. 13R): The Device for females' right Rim's Outer Edge, in close up with its Inner Edge on the Conforming Mesh, allowing suction from the Vacuum Ability to flow through it and out.

(FIG. 25, Ref. A): An illustration of The Vacuum Ability's suction occurring through the Conforming Mesh at The Device for males' right side Vacuum Port.

(FIG. 25, Ref. 44R): An illustration of The Device for males' right side Vacuum Port (VP) on the Conforming Mesh (CM).

(FIG. 25, Ref. 16): The Device for males' right side Rim's Inner Edge, in close up on the Conforming Mesh, allowing suction from the Vacuum Ability to flow through it and out, so that it may comfortably conform to a wearer's breast.

(FIG. 25, Ref. 17): The Device for males' right side Rim's Outer Edge, in close up with its Inner Edge on the Conforming Mesh, allowing suction from the Vacuum Ability to flow through it and out.

SEQUENCE LISTING

Not Applicable

The invention claimed is:

1. A brassiere style breast imaging device comprising:
a distinct left portion and a distinct right portion that resembles a full brassiere when coupled, each portion with a shoulder attachment at top, a wide wrap-around piece with hook and loop fasteners connected to a rim on each distinct portion,
wherein the left portion has a first coupling piece at a middle center of a left rim,
wherein the right portion has a second coupling piece at a middle center of a right rim;
wherein each distinct portion includes a conforming material that is adapted to envelop a breast and form the cups or mold sizes;
wherein the conforming material comprises a plurality of sensors of varying sizes connected throughout by flexible wires called mesh lines configured to send and receive information about a person's breast matter;
wherein the conforming material comprises an outer layer and an inner layer;
wherein both the inner layer and the outer layer are soft and flexible;
wherein the sensors and the mesh lines rest upon or are contained within the conforming material;
wherein the inner and outer layer are connected at the rim and are configured to pass air between the layers;
wherein a vacuum port is located near a bottom section of the conforming material and the rim;
wherein the rim is soft and pliable and can be pushed, pulled, adjusted or crimped without losing its airtight properties;
wherein the vacuum port is adapted to receive a small flexible hose;
wherein the hose is configured to be used with a vacuum device;
wherein the hose is configured to remove air through the rim from between the connected inner and outer layers causing a flow of suction to occur and the device to be pulled towards the breast;

wherein the shoulder attachments are soft, long, wide and flexible and are configured to be manipulated and hold the Device on a person's shoulders;

wherein the first coupling piece at the middle center on the left rim comprises a rectangular opening;

wherein the second coupling piece at the middle center on the right rim comprises a triangular strip with hook and loop fasteners and is adapted to fit through the first coupling piece on the left rim to close the Device together;

wherein the Device further includes a grounding point with an attached wire or cable on each left and right side shoulder attachments;

wherein the grounding point wire or cable is configured to transmit data, wherein the grounding point wire or cable is connected to the mesh lines;

wherein a left grounding point wire is connected to left mesh lines and a right grounding point wire is connected to right mesh lines;

wherein the grounding point wire or cable is configured to ground the Device for safety;

wherein the Device has a section that allows a physical and/or wireless data interchange via computer or computation device;

wherein the section that allows the Device to be physically connected to a computer or computation device is a data port;

wherein the Device further includes large, wide, garment-like rectangular piece with hook and loop fasteners for Device elongation;

wherein the entire Device is capable of being adjustable in size and can be disposable or reusable.

2. A breast plate style breast imaging device comprising:

a distinct left portion and a distinct right portion that resembles a full breast plate, each portion with a shoulder attachment at top, a wide wrap around piece with hook and loop fasteners connected to a rim on each distinct portion;

wherein the left portion has a left rim, wherein the right portion has a right rim;

a narrow opening in between the left rim and the right rim;

wherein each distinct portion includes a conforming material that is adapted to envelop the breasts and torso to form the cups or mold sizes;

wherein the conforming material comprises a plurality of sensors of varying sizes connected throughout by flexible wires called mesh lines configured to send and receive information about a person's breast matter;

wherein the conforming material comprises an outer layer and an inner layer;

wherein both the inner layer and the outer layer are soft and flexible;

wherein the sensors and mesh lines rest upon or are contained within the conforming material;

wherein the inner and outer layer are connected at the rim and are configured to pass air between the layers;

wherein a vacuum port is located near a bottom section of the conforming material and the rim;

wherein the rim is soft and pliable and can be pushed, pulled, adjusted or crimped without losing its airtight properties;

wherein the vacuum port is adapted to receive a small flexible hose;

wherein the hose is configured to be used with a vacuum device;

wherein the hose is configured to remove air through the rim from between the connected inner and outer layers causing a flow of suction to occur and the device to pulled towards the breast;

wherein the shoulder attachments are soft, long, wide and flexible and are configured to be manipulated and hold the Device on a person's shoulders;

wherein the Device further includes a grounding point with an attached wire or cable on each left and right side shoulder attachments;

wherein the grounding point wire or cable is configured to transmit data, wherein the grounding point wire or cable is connected to the mesh lines;

wherein a left grounding point wire or cable is connected to left mesh lines and a right grounding point wire or cable is connected to right mesh lines;

wherein the grounding point wire or cable is configured to ground the Device for safety;

wherein the Device has a section that allows a physical and/or wireless data interchange via computer or computation device;

wherein the section that allows the Device to be physically connected to a computer or computation device is a data port;

wherein the Device further includes large, wide, garment-like rectangular piece with hook and loop fasteners for Device elongation;

wherein the entire Device is capable of being adjustable in size and can be disposable or reusable.

\* \* \* \* \*